United States Patent [19]
Karlsson et al.

[11] Patent Number: 5,520,191
[45] Date of Patent: May 28, 1996

[54] MYOCARDIAL ISCHEMIA AND INFARCTION ANALYSIS AND MONITORING METHOD AND APPARATUS

[75] Inventors: Per Karlsson, Taby; Gunilla Lundahl, Lidingo; Michael Oljemark, Saltsjo-Boo; Johan Ubby, Vaxholm, all of Sweden

[73] Assignee: Ortivus Medical AB, Taby, Sweden

[21] Appl. No.: 320,511

[22] Filed: Oct. 7, 1994

[51] Int. Cl.⁶ .................................................. A61B 5/0472
[52] U.S. Cl. .......................................... 128/702; 128/699
[58] Field of Search ..................................... 128/696, 699, 128/702, 703, 704, 705, 710; 607/25; 364/413.06

[56]         References Cited
           U.S. PATENT DOCUMENTS 3,548,813 12/1970 Berner.
3,858,034 12/1974 Anderson.
5,038,800  8/1991 Oba ........................................ 128/904

Primary Examiner—William E. Kamm
Assistant Examiner—Scott M. Getzow
Attorney, Agent, or Firm—Cooper & Dunham

[57]              ABSTRACT

A cardiac monitoring method and system provides advanced ischemia and infarction analysis and monitoring. Advanced calculations are performed on ECG signals to obtain parameter values relating to myocardial ischemia and infarction. Dominant heart beats are averaged to form a smooth beat, which is analyzed to determine the parameter values continuously and in real-time. The result of each analyzed time interval is presented as points in a trend graph on a monitoring display. All calculations are performed on-line and the trend curves are updated immediately.

20 Claims, 11 Drawing Sheets

MYOCARDIAL ISCHEMIA AND INFARCTION ANALYSIS AND MONITORING METHOD AND APPARATUS

BACKGROUND OF THE INVENTION

1. Field of the Invention

The present invention relates to cardiac monitoring systems and, more particularly, to cardiac monitoring systems which provide an analysis and display of parameters relating to the condition of ischemic patients.

2. Description of the Related Art

A number of new clog dissolving agents presented by the pharmaceutical industry during the past couple of years have given cardiologists the ability to immediately treat acute myocardial ischemias through chemical thrombolytic therapy. However, it is frequently difficult to properly control and adjust such therapy during the acute phase of a myocardial ischemia. Known methods are either expensive or have too large a delay (up to several hours) between the time of the myocardial ischemia time and the presentation of the results.

Some cardiac monitoring systems and methods also utilize a known 12-lead ECG in which ECG signals are displayed directly on a monitor in real-time. Such a 12-lead ECG arrangement has the disadvantages that a large number of electrodes must be placed on the patient in positions which cover mainly the frontal parts of the myocardium. A large storage capacity is also required in order to record all the ECG signals from the electrodes. However, many doctors are familiar with the format of the 12-lead ECG.

SUMMARY OF THE INVENTION

The present invention constitutes a substantial improvement in cardiac monitoring systems, and in particular, an improvement in cardiac monitoring systems providing an analysis and display of parameters relating to the condition of ischemic patients.

It is an object of the present invention to overcome the aforementioned disadvantages of known cardiac monitoring systems.

In particular, it is an object of the present invention to provide real time parameters describing the acute condition of the myocardium during thrombolytic therapy in the initial phase of myocardial infarctions.

In particular, it is an object of the present invention to provide a cardiac monitoring system in which the ECG signals are represented by three perpendicular leads which are continuously averaged and stored in equal intervals and then later displayed in the format of a dervied standard 12-lead ECG.

It is also an object of the invention to continuously store the three perpendicular leads, X, Y and Z, and recalculate the signals therefrom in order display a derived standard 12-lead ECG in real-time.

It is also an object of the invention to provide an improved method to be used in pharmaceutical studies to verify the actual benefits of new drugs.

It is a further object of the invention to provide an improved monitoring method to be used during different kinds of coronary operations, such as PTCA—coronary artery balloon dilatation, or other procedures requiring an accurate real-time analysis and monitoring.

The method in a preferred embodiment of the present invention presents the required information in real-time using advanced calculations on ECG signals to obtain "simple" parameter values describing the myocardial ischemia (lack of oxygen) and the course of infarction. Eight standard ECG surface electrodes are placed on the patient according to the Frank electrode system developed in the 1940s. The signals in the eight leads are processed in a known manner to form the ECG vector which can be described by three perpendicular leads: X, Y, and Z. These three leads contain all the information necessary to describe the ECG completely.

ECG changes are continuously analyzed to reflect the course of ischemia and infarction based on vector-cardiography. All dominant beats are continuously acquired for the analysis and averaged at even intervals to form one very smooth beat, suitable for high definition calculations. Those intervals may range from ten seconds up to four minutes. The first averaged beat is used as an initial reference beat. All succeeding, averaged beats will be compared to this initial beat to plot the changes.

The resulting, averaged beat is analyzed to form a plurality of parameters. The ST vector magnitude (ST-VM) measures the offset of the ST-segment and is commonly accepted as a measure of ischemia in the myocardium. The change of the ST magnitude compared to the initial reference beat (when monitoring was started) (STC-VM) is also calculated. The QRS vector difference (QRS-VD) measures changes in the QRS complex compared to the initial ECG and reflects the change in morphology of the QRS complex compared to when monitoring was started. The QRS-VD parameter has been linked to the course of the myocardial infarction in several studies.

The invention displays the result of the advanced analysis from every time interval as a new point in very simple trend graphs lo that are continuously updated. All calculations are performed line so the trend curves are updated immediately. The fundamental advantage of this method is that every complex and subtle information from the ECG signals is analyzed and processed to finally form simple parameter values which are displayed in simple trends. Since the result is presented in the simple graphical form of a trend over time, it is perfect for on-line monitoring and the trend curves provide immediate information on the degree of ischemia or the course of an ischemia. A change in the condition of the heart may even be visible on the display before the patient undergoes pain.

Since the average ECG is always stored, the original ECG of every point of the trend curve may always be displayed as either a derived 12-lead ECG, the X, Y and Z leads, vector magnitude or vector loops. When a patient is monitored, the acquired information is permanently stored in the central workstation of the system. The information may be copied onto recording media, such as a 3.5" floppy disk, and subsequently analyzed for clinical or scientific purposes.

DETAILED DESCRIPTION OF THE PREFERRED EMBODIMENTS

Figure 7:
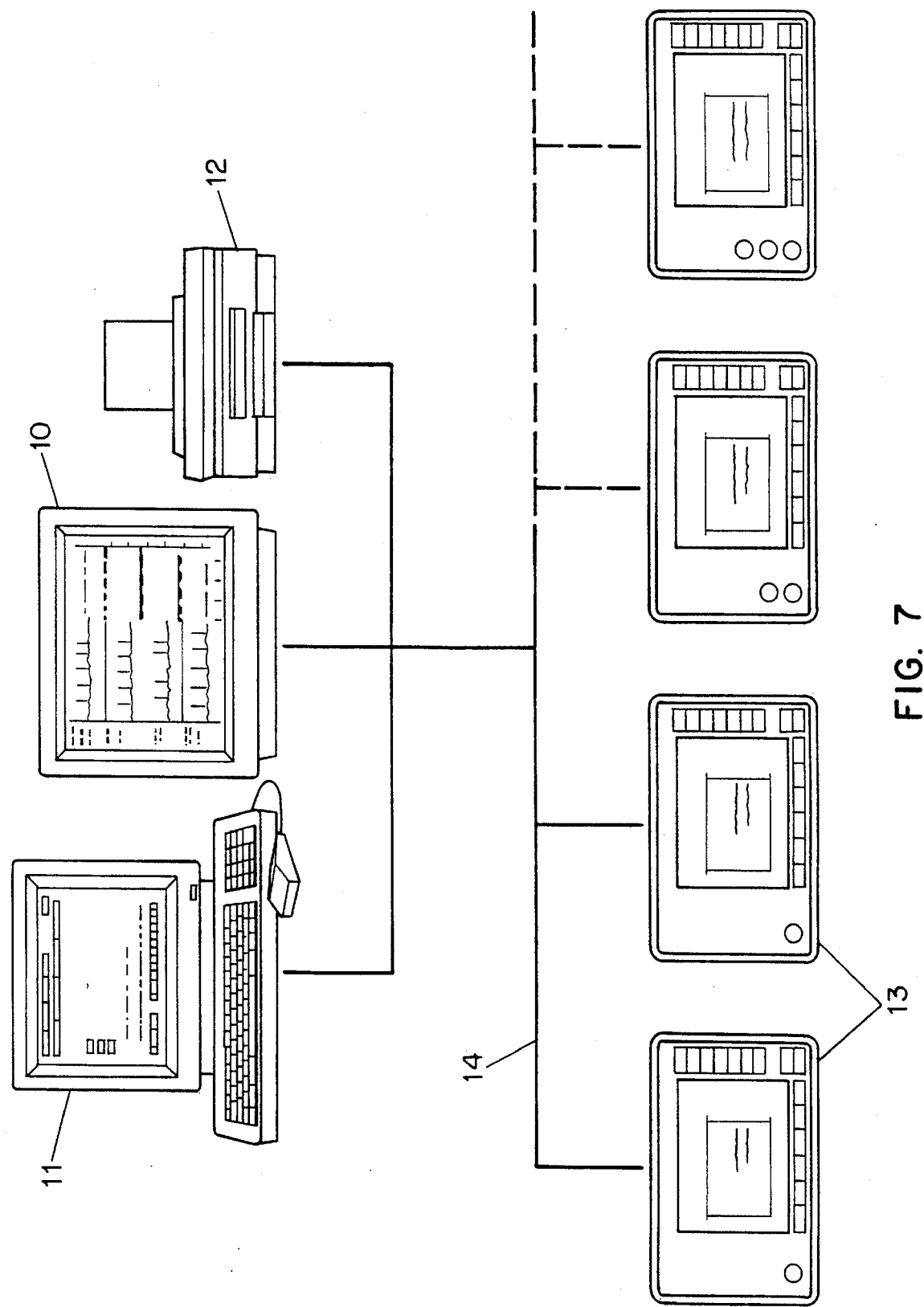
FIG. 7 is a diagram illustrating elements of the system in a first embodiment of the invention.

FIG. 7 shows the setup of the system in a first embodiment of a system utilizing the invention. It consists of at least one central monitoring unit 10, a central workstation 11 for controlling the system, including the display on the central monitoring unit(s), and for storing data, a laser printer 12 and a plurality of bedside monitors 13, one for each patient. All of the units communicate via an Ethernet network 14.

Processing functions are divided between central workstation 11 and each bedside monitor 13. The distributed intelligence ensures maximum system reliability and offers both powerful traditional monitoring and advanced ischemia monitoring.

Figure 12:
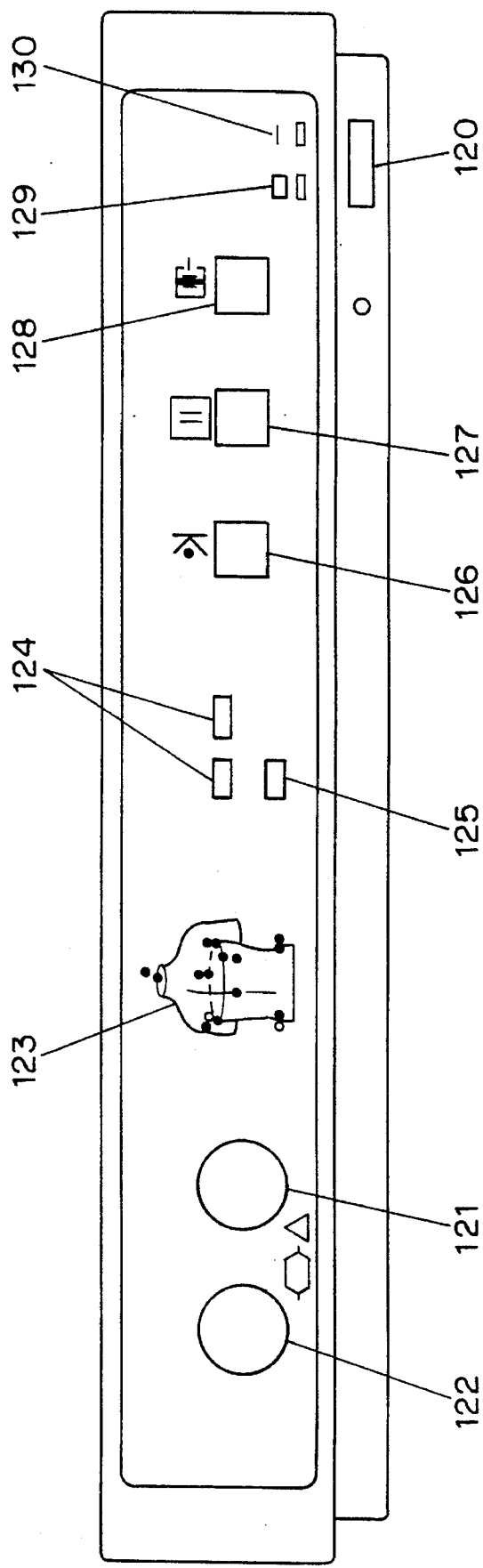
FIG. 12 shows the front face of an acquisition module used in a second embodiment of a system employing the invention.

Each of the bedside monitors 13 combines multilead arrhythmia analysis with new, advanced ischemia monitoring features and does all the calculations for the ECG analysis, presents the information on the display and transmits it over Ethernet network 14 to a central processing unit in the workstation 11. FIG. 12 shows the front face of an exemplary bedside monitor 13. In addition to the ECG analysis, each bedside monitor 13 is also available with a number of options, such as non-invasive blood pressure, pulse oximetry, dual invasive pressures and dual temperatures, and is operated simply by touching the self-instructive menus on the front of the monitor. Analogue ECG outputs on the back of the bedside monitors allow connection to other medical equipment.

Eight ECG leads are used for improved sensitivity of the analysis of both arrhythmias and ischemia. With information from all eight leads, the ischemia analysis is able to reflect ischemic changes from the entire myocardium. The ischemic evolution over time is presented in a trend graph that is continuously updated on the display. The trend graph may include up to 8 days of continuous monitoring. With four traces and a trend graph, a waveform may be displayed for every physiological parameter in addition to the vital trend graphs. (For patients without ischemic symptoms, 4 leads can be used for monitoring.)

The averaged beats in the form of the X, Y and Z leads are automatically calculated and stored every minute. From these signals a dervied 12-lead ECG may be reviewed on the bedside monitor at any time during the monitoring session.

The central workstation can automatically identify up to six different functions (MIDA, HR/PVC, $SpO^2$, NIBP, IBP and Temp for example) in each bedside monitor and all of the physiological information acquired by the bedside monitors can be transferred for examination and storage at the workstation. The monitoring functions controllable by the central workstation will thus vary depending on the configuration of the bedside monitors connected to the central workstation. For example, central workstation 11 may provide conventional ECG monitoring, arrhythmia monitoring, ischemia monitoring with parameters reflecting the ECG changes in clear trend graphs, averaged derived 12-lead ECG display, 24-hour full disclosure arrhythmia of all monitored patients, 24-hour continuous 12-lead ECG display derived from the continuously stored X, Y, and Z leads for all monitored patients and monitoring of any and all non-ECG functions monitored on the bedside monitors such as $SpO^2$, NIBP, BP and Temp.

Figure 8:
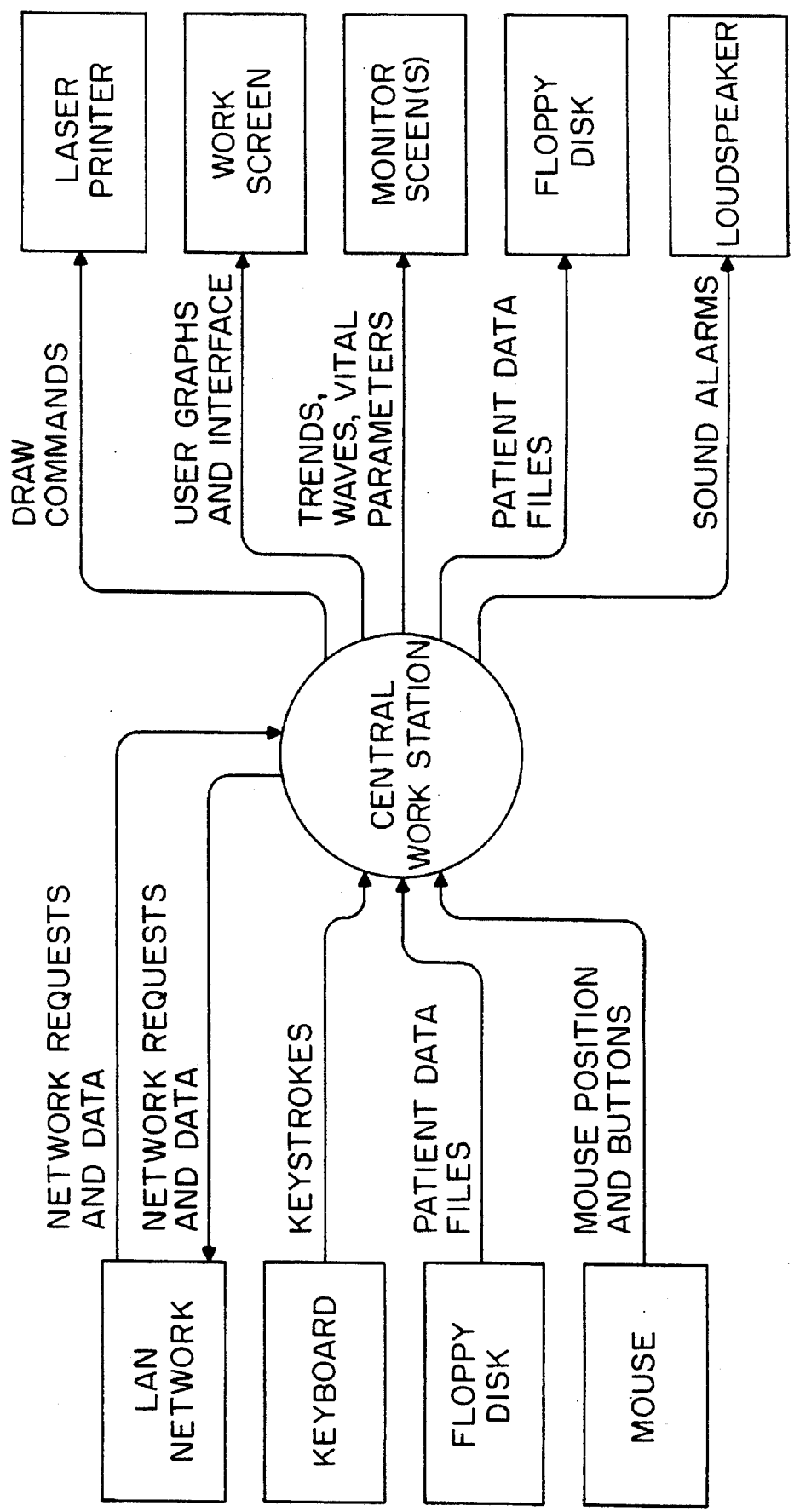
FIG. 8 is a block diagram graphically illustrating the connection of the central workstation to other components of an apparatus employing the invention.
Figure 13:
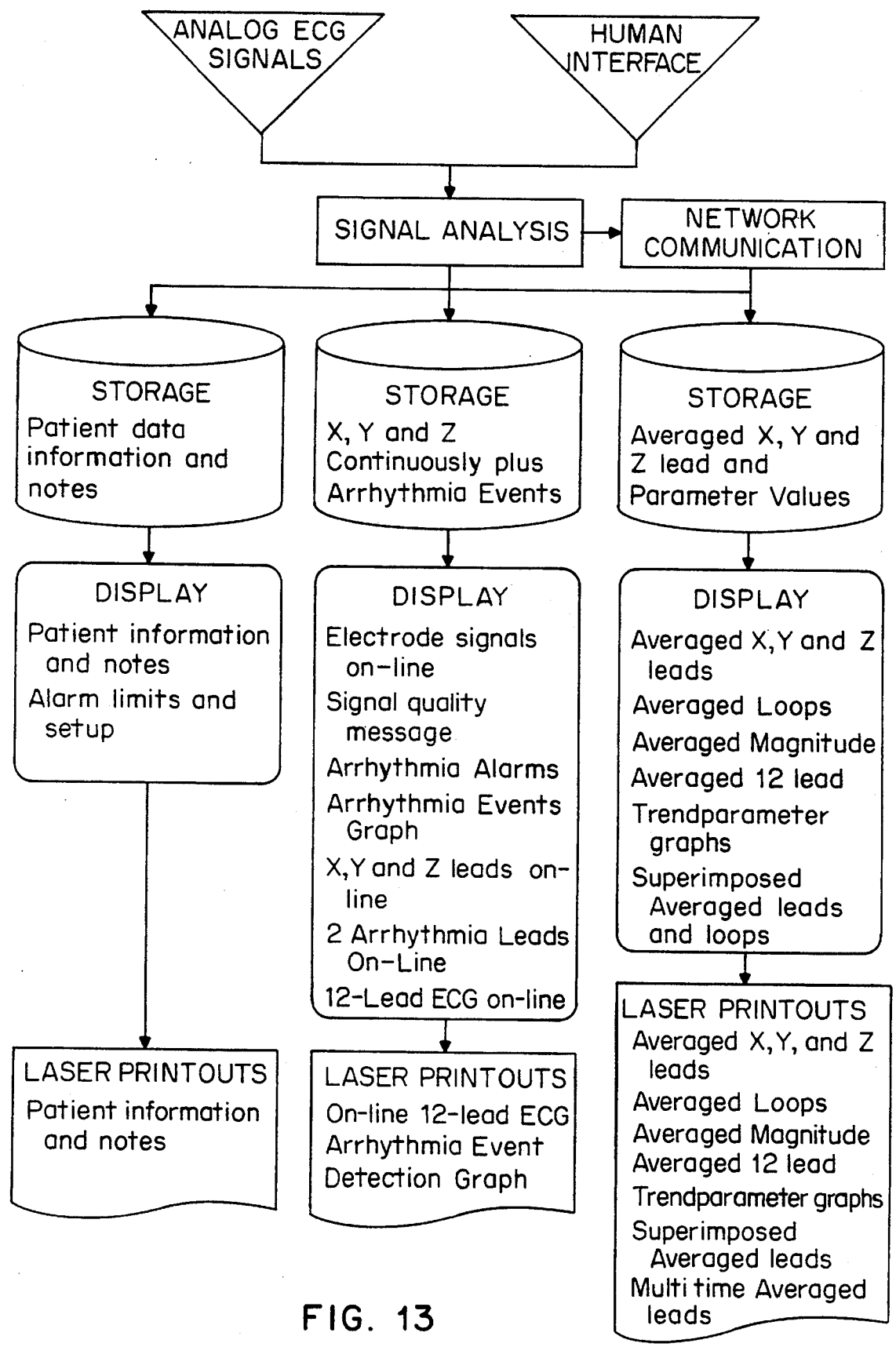
FIG. 13 shows the overall input/output possibilities in an apparatus employing the invention.

The central workstation is preferably a networking personal computer operating with specialized menu-driven applications software. An exemplary connection of the central workstation to other components is shown in FIG. 8 and an exmplary illustration of the functions which may be performed is shown in FIG. 13. The central workstation provides a straightforward and simple user interface operated through the selection of "keys" in a graphical display. Each key has an instructive text or symbol describing the function of the key. A mouse (or other pointing device) is used to point to and select a desired key. (In the examining functions, the mouse is also used to point out the ECGs to be enlarged, etc. ) The surface of a key is normally grey. However, active keys are made yellow and void keys that cannot be accessed are dark grey.

Figures 9, 10:
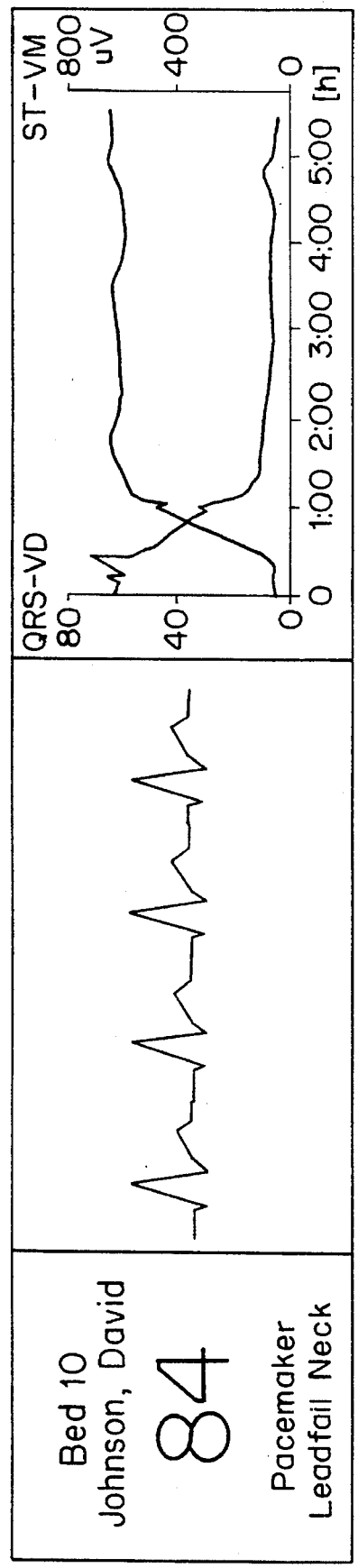
FIG. 9 is a diagram showing the top part of a graphical interface display which appears on the central workstation of a system employing the invention.
FIG. 10 is a diagram showing an example of the display format used for monitoring each patient on a central monitoring unit.
Figure 11:
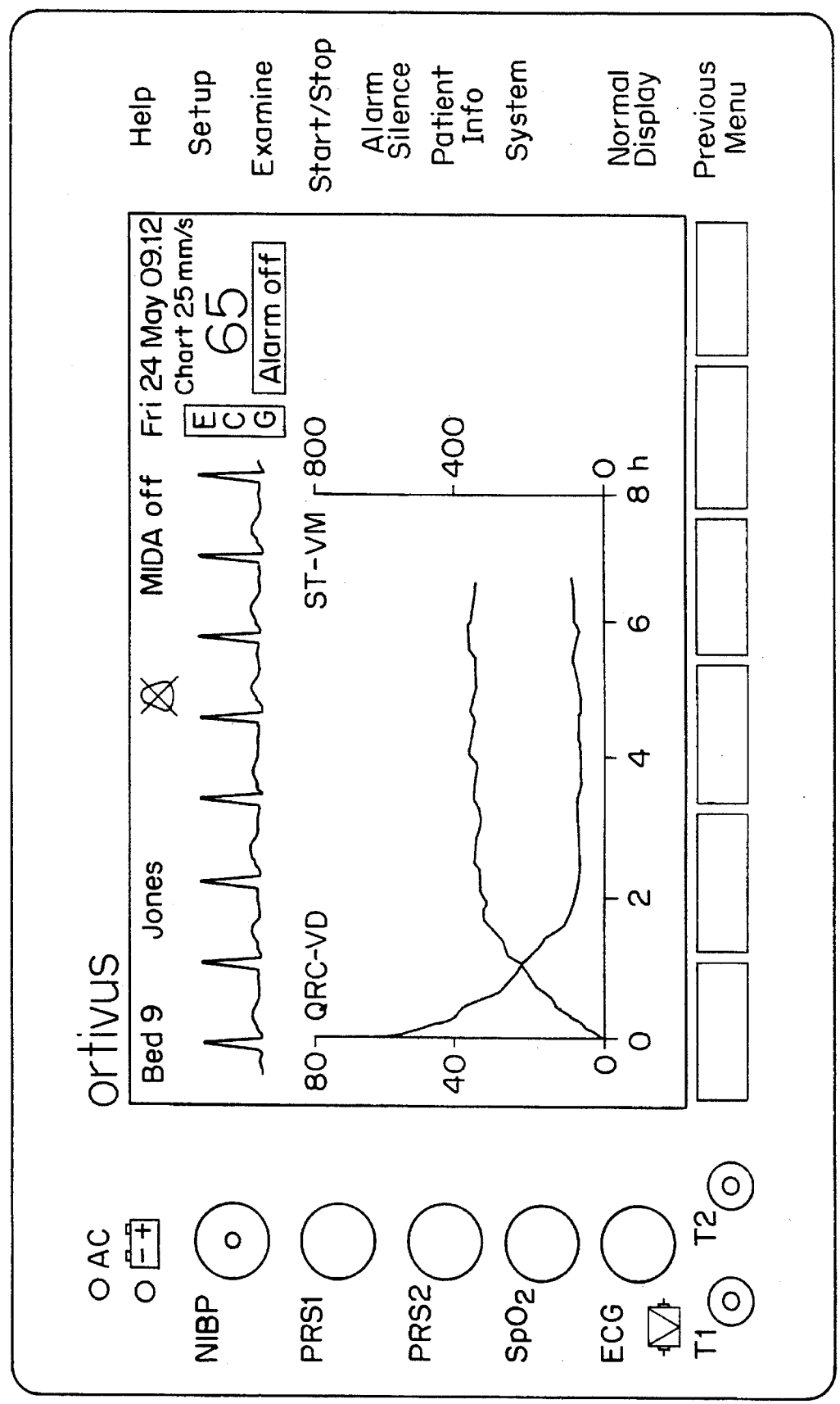
FIG. 11 shows the front face of a bedside monitor used in a first embodiment of a system employing the invention.

FIG. 9 shows an example of the initial menu displayed in an upper portion of the display in a preferred embodiment of the invention. There are two rows of keys. The keys in the top row are labeled with numbers corresponding to each one of a number of patients, System, signal Status and Stored Patients. The lower row of key preferably contains key commands for examining a patient file. For example, the keys may be labeled as Patient Info, Alarm, Report, Trend, ECG & VCG, Arrhythmia Events, ECG MIDA, ECG Review, All Leads and Setup. The keys are used to select and control all functions, both on the central monitors and on the workstation itself.

Signal status messages are displayed on the display of the workstation if no central monitor is in use. (Otherwise, signal status messages are always displayed on the central monitor.) A red patient key is used to indicate that something is wrong, that there is bad signal quality or problem with the analysis or other errors. If so, the reason may be seen in the Signal Status function. A crossed over key is used to indicate that the analysis has paused. The actual message for a specific patient is then displayed to the right of the patient name in the upper part of the workstation display.

CENTRAL MONITORING UNITS

All parameters available to the central workstation may be displayed as trend graphs on one or more central monitoring units 10. The central monitoring unit(s) 10 display the "live" situation of a plurality of patients simultaneously. The central monitoring units are preferably large (e.g., 17- or 21-inch), high-resolution computer monitors such as that shown in FIG. 7. Software display drivers in the workstation utilize high resolution graphics and the display is preferably at least 1024×768 pixels resolution. The monitors may continuously and simultaneously monitor ECG waveforms, vital parameters, alarms and vital ischemia trendings for each of a number of patients.

Arrhythmia alarms are presented in red letters on the displays and a 24-hour full disclosure arrhythmia review function offers complete control and documentation of all arrhythmias. The central monitoring unit(s) 10 also enable examination of derived 12-lead ECGs of every minute monitored. All other functions are displayed and controlled on workstation.

The information on the monitors is fixed in order to always present the current status of all patients. All interactive functions and examination of patient data which appears on the monitors is controlled from the workstation. The left half of the monitor screen presents conventional monitoring including heart rates and patient information, waveforms, arrhythmia alarms and optional vital signs while the right-hand side presents the ischemia trends. The graphs display the ischemic evolution of each monitored patient starting from a designated time, such as the patient's admission. The graphs are continuously updated to always include the most recent values. Up to six patients may be monitored on each display. When more than four patients are monitored, additional monitors may be used. The network 14 allows the selection of any two waveforms from each bedside patient monitor to be displayed on the central monitor. The waveform selected to be displayed on the central monitor need not be the same waveform selected for display on the corresponding bedside monitor 13. An example of a trend graph displayed on the central monitor for a single patient is shown in FIG. 10. The signal status and MIDA messages are identical to the ones displayed in the signal Status overview of the display for the central workstation discussed later.

The content of the display of a respective patient on the central monitors (leads, filters, size and speed) is selected by central workstation 11 in the manner described below. The same information is always displayed at the same location in the display for improved functionality. The left side of the display contains bed number 101, patient name 102, heart rate 103, pacemaker information 104 and signal status message 105. The right side of the display contains trend graph(s) 106 and MIDA recording status message 107.

A patient is chosen for detailed examination and/or monitoring by clicking the number key corresponding to the patient in the top row of keys on the Workstation.

The Setup Menu key is selected to adjust the patient's display. If the Monitored ECG Lead key of the Setup Menu is selected, then a picture is displayed which contains the waveform for each of the patient leads along with a respective corresponding key, as well as keys for selecting the filtering, curve size and sweep speed of the displayed waveforms. If waveforms other than ECG leads, such as $SpO^2$ and PA pressure, are monitored, then these appear in the display as well and are controlled in the same manner as the ECG leads. The primary waveform to be displayed on the central monitor is selected by clicking the corresponding key.

The setup menu in the first embodiment displays three filter keys which enable the displayed waveform to be filtered for improved visual impression The first key "None" displays the waveform unfiltered. The second key is labeled "0.05–100 Hz" and gently filters the curve from baseline variations below 0.05 Hz and noise above 100 Hz. The third key is labeled "0.5–40 Hz" and filters the displayed curve from baseline variations below 0.5 Hz and noise above 40 Hz.

The setup menu in the preferred embodiment also displays three ECG size keys which set the size of the displayed waveform. When the "Auto" key is selected, the size of the displayed curve is continuously adopted to fill two thirds of the height available for the curve. The adoption is very slow so that if the original amplitude of the curve slowly decreases (maybe due to necrosis), the automatic adoption may result in an unaffected curve on the monitor. The "10 mm/mV" key sets the amplitude of the displayed curve to 10 mm/mV. The "20 mm/mV" key sets the amplitude of the displayed curve to 20 mm/mV.

All curves on the central monitor have the same speed. The speed may be set to 25 mm/sec or 50 mm/sec via selection of the appropriate key.

For all patients, a second monitoring curve (additional ECG, pulseoximetry or pressure) may also be selected for display in addition to the primary curve. This function is controlled by selection of a key marked "On/Off" which appears under the header "2nd wave" in the setup menu display. Selecting the On/Off key activates the second curve. A key marked "Wave 1" is selected to enable control of the upper curve (lead, filter, etc.). A key marked "Wave 2" is selected to enable control of the lower curve.

The Patient Info key allows inputting of the patient's name, ID, original symptoms and physician comments. The information is entered on respective lines using the keyboard in typewriter fashion and then pressing the enter key. The Patient Info menu also contains a Pacemaker key which is selected to indicate that the patient has a pacemaker.

The menu also has an Add note feature which permits the entering of notes and observations at the workstation at any time. When the Add note key is selected, a field is opened at the bottom of the display, the time is automatically displayed, and the Add note key is changed to a Save note key. The text of the note is entered and edited using the keyboard.

The note is saved by clicking on the Save Note key. If the patient's waveforms are stored for subsequent analysis, the system stores all notes as well. They may be reviewed and printed on paper at any time.

The Patient Info menu is closed by selecting either a Save Patient Info key or a Cancel key. When a patient is discharged from the bedside monitor, the central workstation stores all recordings, including 24-hour full disclosure arrhythmia, by default until the storage capacity is needed for new recordings. When capacity is full, the oldest recordings will be erased automatically.

Once the patient has been entered into tho system as described above and the display for the central monitor hag been formatted as described above, the system then commences on-line myocardial ischemia dynamic analysis and monitoring (MIDA) for treating patients with myocardial infarction, unstable angina or when monitoring patients during and post-PTCA.

Figure 4:
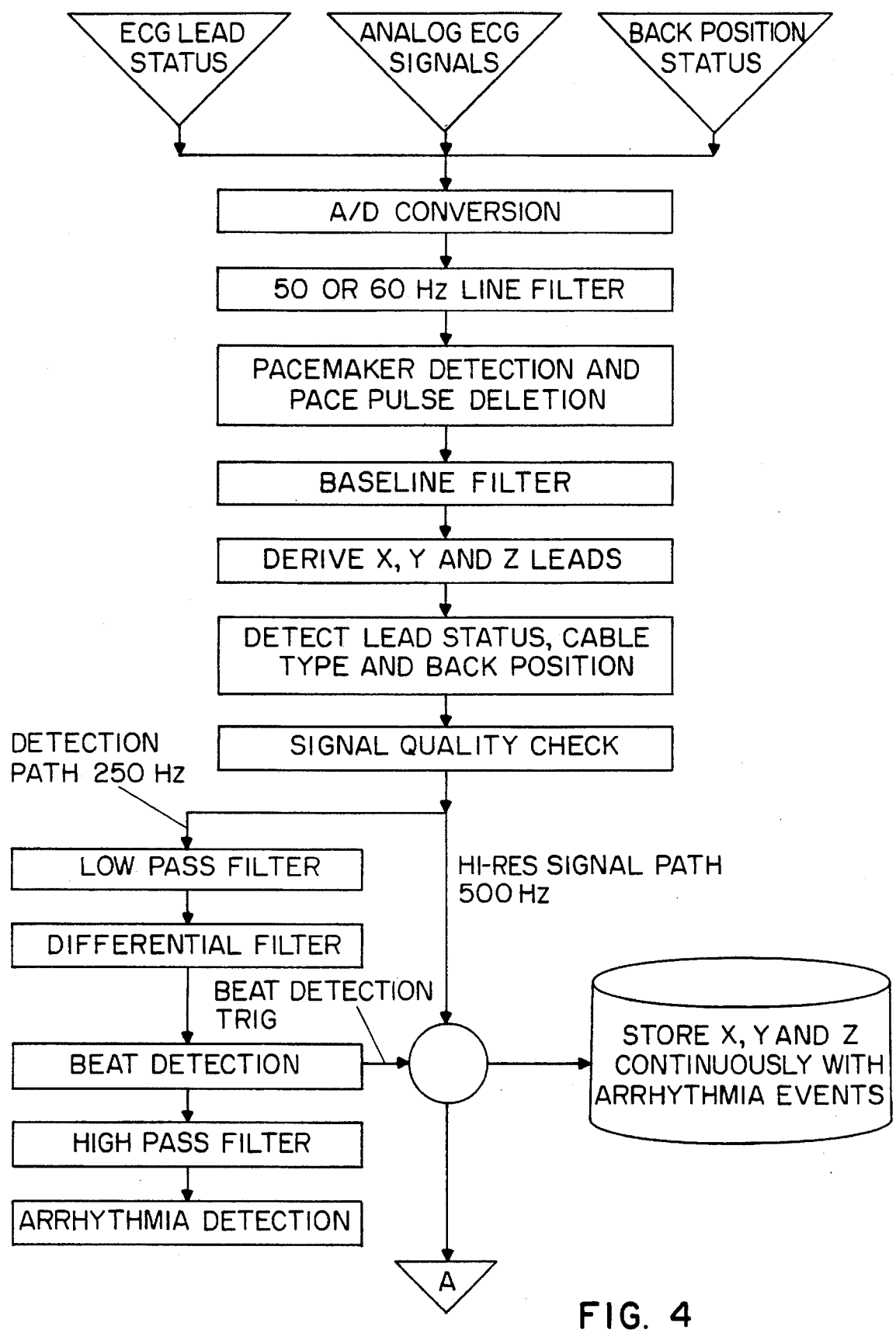
FIG. 4 is a flowchart depicting the manner in which three perpendicular leads (X, Y, and Z) are produced in a preferred embodiment of the invention.

Based on the electrical signals from eight ordinary surface ECG electrodes placed according to Frank, three perpendicular leads (X, Y, and Z) are produced in the manner shown in FIG. 4. The method used in the system permits ischemia monitoring based on Frank leads, analyzing the X, Y, and Z signals to achieve unique parameters, such as ST-VM, QRS-VD and STC-VM, which are displayed in a trend chart.

Figure 5:
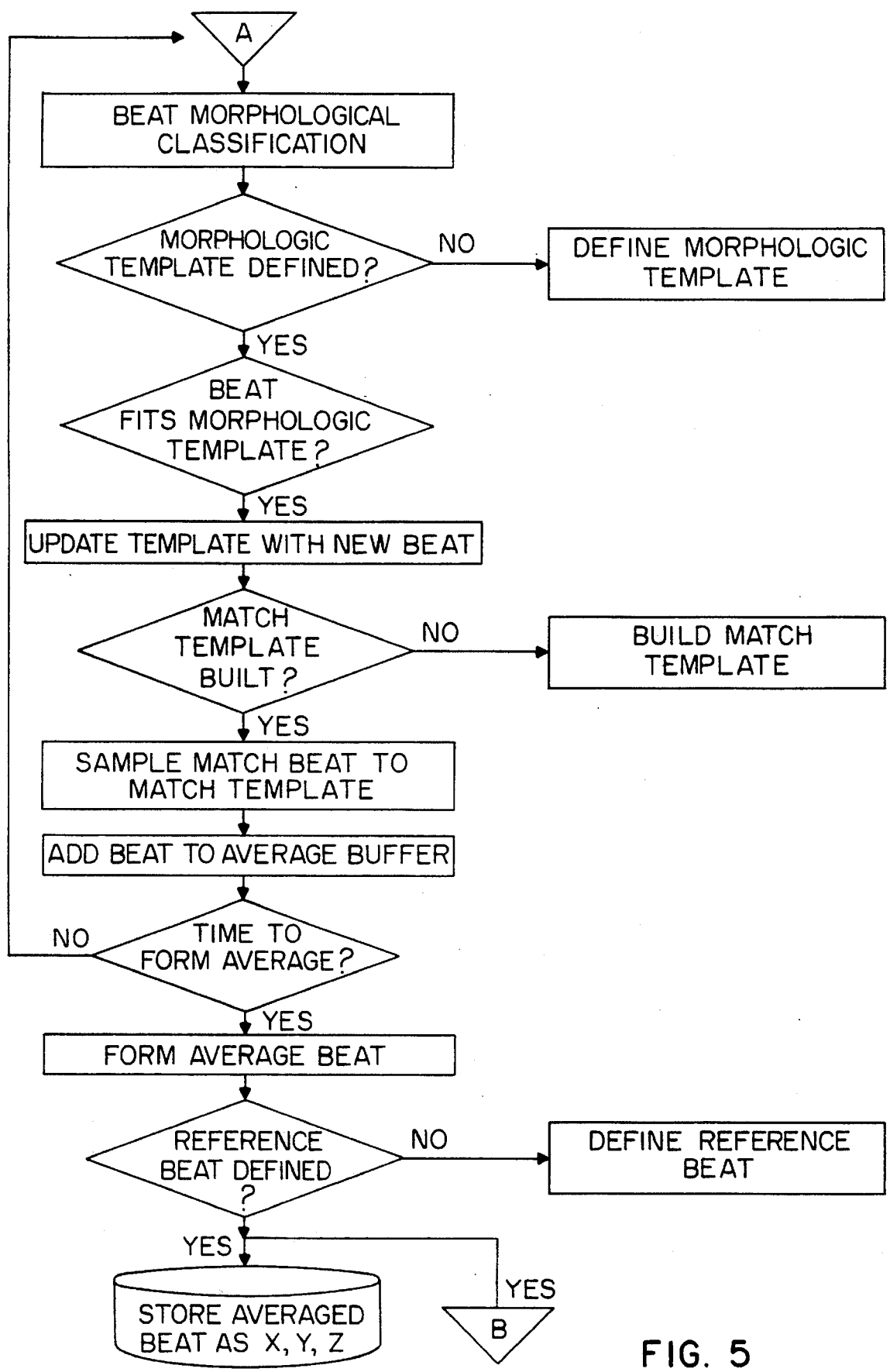
FIG. 5 is a flowchart showing the initial steps in the analysis and monitoring used in the preferred embodiment of the invention.

When monitoring starts in the manner shown in FIG. 5. Beats undergo a morphological classification and a morphologic template is defined. If a beat fits the morphologic template, a match template is built, such by selecting a normal ECG beat to serve as the template. Beats are compared to the morphologic template to determine which beats are "normal" beats that should be included in the analysis and which beats should be excluded from the MIDA analysis. During the remainder of the analysis, the three leads X, Y and Z are continuously scanned for "normal" beats. When a normal beat is found, it is matched and included in an average of the acquired normal beats formed at even time intervals, preferably every minute provided that the quality of the signal is sufficient. The ECG from the first average beat is referred to as the Reference complex and used as a reference to which the ECGs from all subsequent beats are compared to see the relative change over time.

Figure 6:
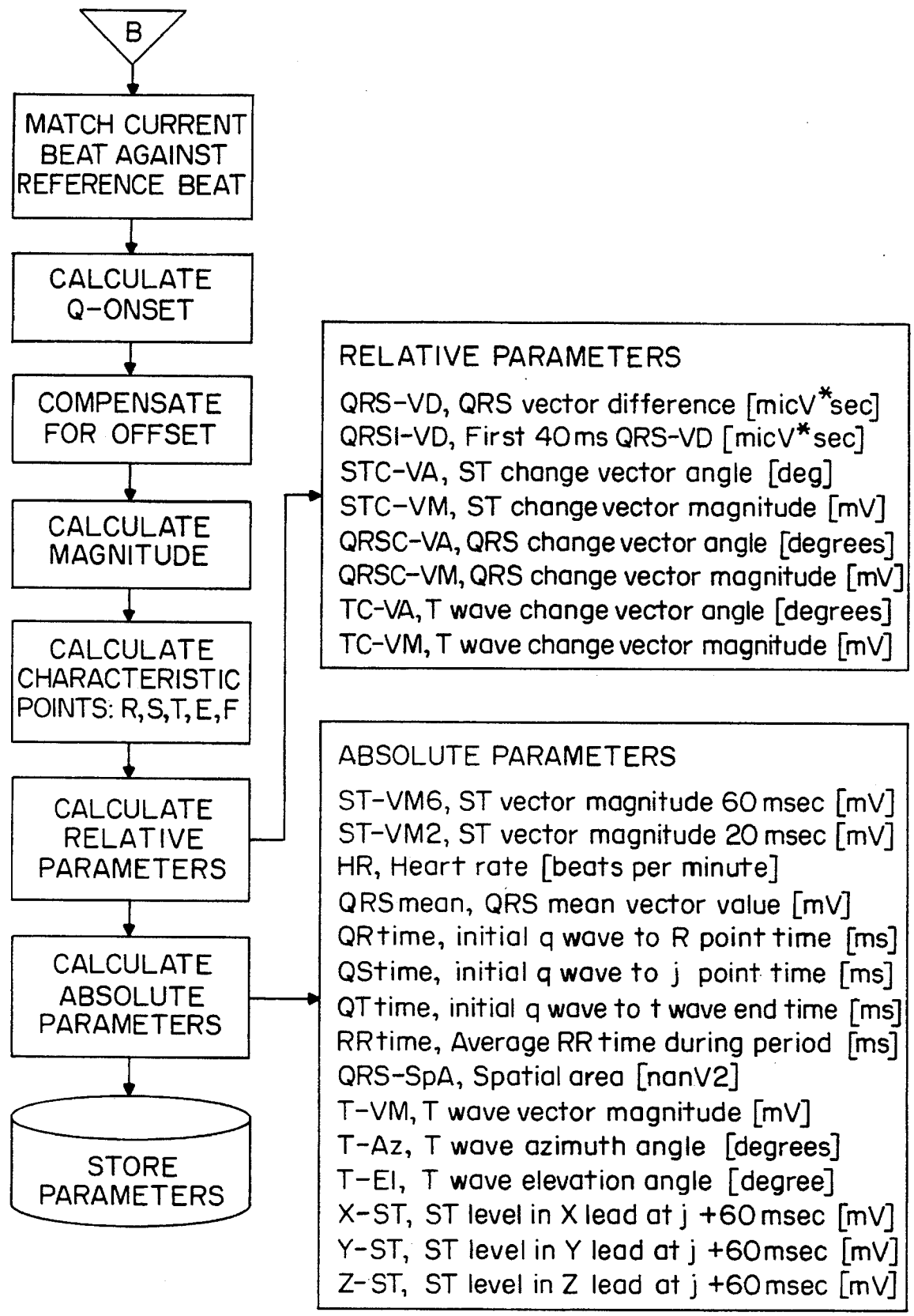
FIG. 6 is a flowchart depicting the manner in which the averaged beat, represented by the averaged X, Y and Z leads, undegoes advanced calculations to determine parameters describing the condition of the ECG.

At even time intervals between a range of 10 seconds and 4 minutes, the averaged beat, represented by the averaged X, Y and Z leads, undegoes advanced calculations as shown in FIG. 6 to determine up to thirty different parameters describing the condition of the ECG. The parameters are stored in addition to the averaged ECG itself.

There are two kinds of parameters: absolute and relative. Absolute parameters are calculated from the actual ECG complex itself. Relative parameters are calculated from the difference between the current ECG complex and the initial reference complex to reflect serial cahnges over time.

The following are examples of absolute parameters: QRSmax, QRSmean, ST-VM, ST-VM2, X-ST, Y-ST, Z-ST, QRS-SpA, HR, QRtime, QStime, QTtime, RRtime, T-VM, T-Az, T-El, X-ST, Y-ST, Z-ST and Abnorm.

QRSmax (mV) is the maximum magnitude within the QRS-complex.

QRSmean (mV) is the mean magnitude of the ECG-vector during the time ranging from QRS onset up to QRS end of the initial complex.

Figure 2:
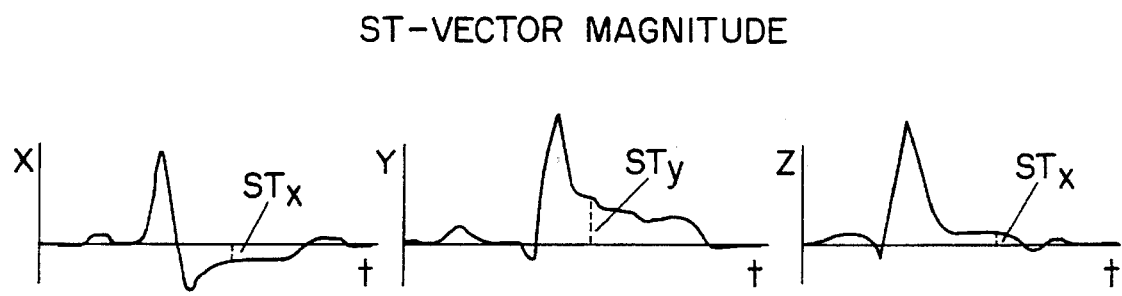
FIG. 2 is a graphical representation illustrating the ST-VM parameter.

The ST vector magnitude (ST-VM) measures the total offset of the ST-segment and is commonly accepted as a measure of ischemia in the myocardium during ischemia. It is measured in every averaged beat, 60 milliseconds after the J point (the end of the QRS complex). The values from the X, Y and Z leads are fed into the formula:

$$ST-VM = \sqrt{ST_x^2 + ST_y^2 + ST_x^2}$$

and the resulting ST-VM value is plotted in the trend graph. The way the formula is constructed, an ST elevation in one lead does not neutralize an ST depression in another lead. Both elevations and depressions are detected simultaneously. See FIG. 2. Since the ST segment is measured in both the X, Y and Z leads, it provides one ST measure that covers the entire heart.

ST-VM2 (mV) is the ST vector magnitude 20 ms after the J point.

X-ST (mV) is the ST level in the X lead 60 ms after the J point.

Y-ST (mV) is the ST level in the Y lead 60 ms after the J point.

Z-ST (mV) is the ST level in the Z lead 60 ms after the J point.

QRS-SpA (nanV$^2$) is the area in the space drawn by the ECG-vector from the point of the initial QRS onset to QRS end.

HR (beats per minute) is the mean value of the heart rate during the MIDA interval.

QRtime (ms) is the time between QRS onset and the maximum magnitude of the current complex.

QStime (ms) is the time between QRS onset and QRS end of the current complex.

QTtime (ms) is the time between QRS onset and the maximum magnitude within the T wave of the current complex.

RRtime (ms) is the mean value of the RR intervals during the averaging period.

The T vector magnitude (T-VM) measures the maximum magnitude within the T-wave of the current complex in mV. The ECG-vector in this point is called the T-vector.

T-Az is the angle of the T-vector in the transversal plane, 0 to 180 degrees from sinister to dexter, and positive if anterior and negative if posterior.

T-El is the angle of the T-vector from the vertical axes, 0 to 180 degrees from dist to cranium.

Abnorm is the number of abnormal beats during the averaging period. All beats that are not classified into the reference class are labelled abnormal.

Figure 3:
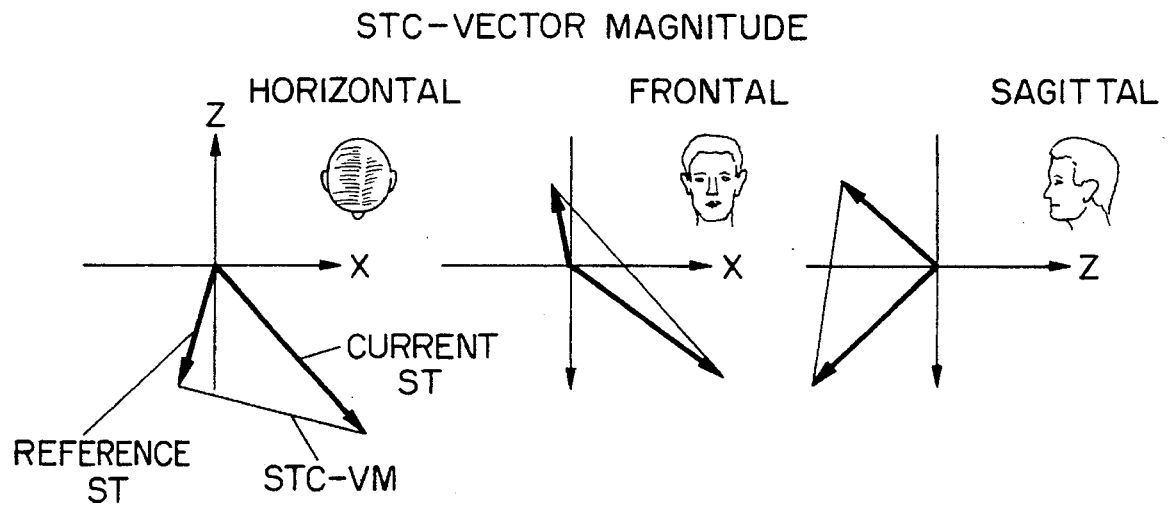
FIG. 3 is a graphical representation illustrating the STC-VM parameter.

The change of the ST magnitude compared to when monitoring was started (STC-VM) is also calculated as shown in FIG. 3. The ST differences are fed into the formula:

$$STC-VM = \sqrt{STC_x^2 + STC_y^2 + STC_x^2}$$

The following are examples of relative parameters: QRS-VD, QRSI-VD, QRSA-VA, QRSC-VM, STC-VA, STC-VM, TC-VA and TC-VM.

Figure 1:
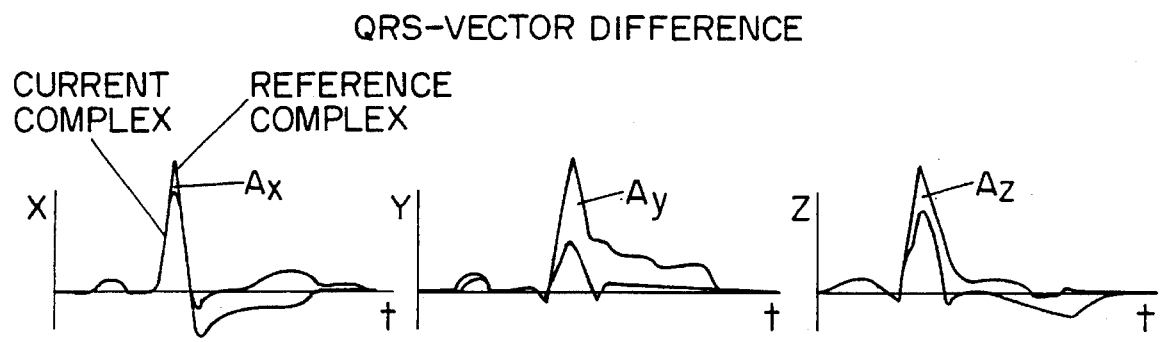
FIG. 1 is a graphical representation illustrating the QRS-VD parameter.

The QRS vector difference (QRS-VD) measures changes in the QRS complex compared to the initial ECG and reflects the change in morphology of the QRS complex caused by, e.g. necrosis and temporary ischemia compared to when monitoring was started. The current QRS complex is compared to the initial QRS complex and the arial difference ($A_x$ in FIG. 1) is calculated in the X, Y and Z leads. The values are fed to the formula:

$$QRS-VD = \sqrt{A_x^2 + A_y^2 + A_z^2}$$

and the resulting QRS-VD is plotted in the trend graph.

QRSI-VD (mVs) is the initial QRS vector difference which is the same as for QRS-VD except that the areas $A_x$, $A_y$, and $A_z$ range from QRS onset of the initial QRS complex and 40 ms forward.

QRSC-VA is the QRS vector angle change and represents the change in the angle between the current and initial QRS vectors. (The QRS vector is the mean vector during the QRS period.)

QRSC-VM (mV) is the QRS vector magnitude change and represents the distance between the initial and current QRS vectors.

STC-VA is the ST vector angle change and represents the change in the angle between the initial and current ST vectors.

STC-VM (mV) is the ST vector magnitude change and represents the distance between the initial and current ST vectors.

TC-VA is the T vector angle change and represents the change in the angle between the initial T-vector and the current T-vector.

TC-VM (mV) is the T vector magnitude change and represents the distance between the initial and current T-vectors.

Selected ones of the relative and absolute parameters describing the course of the ischemia may be chosen for display and plotted in a trend graph. The three most common are the QRS-VD (morphological changes) and ST-VM (st-measurements) and STC-VM (st-changes).

Figure 14:
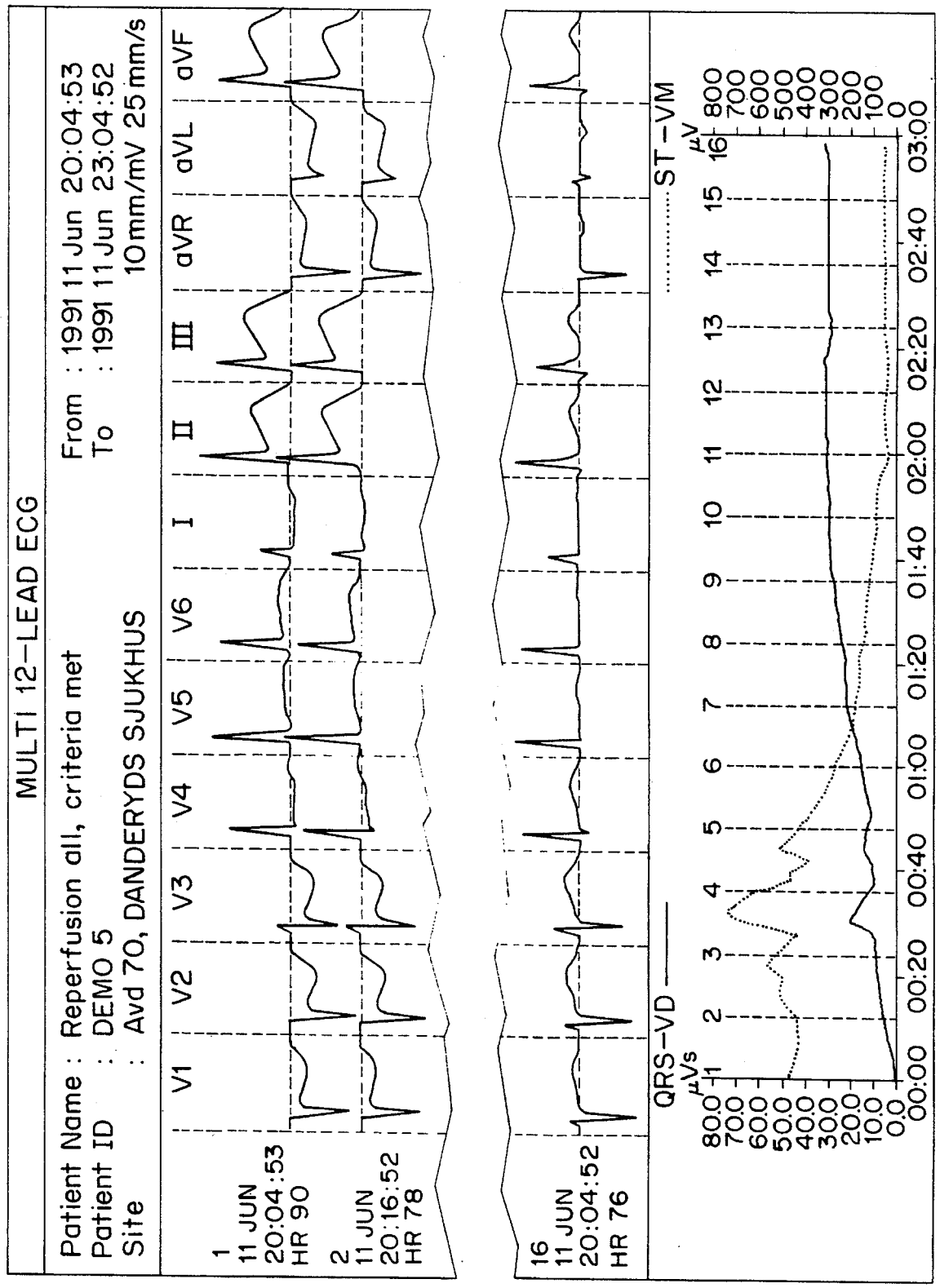
FIG. 14 shows an example of a single page printout, having a plurality of ECG signals printed under each other, produced by the invention.

The averaged ECG that is stored at the end of each time interval contains the values for each of the X, Y, and Z leads. Since the X, Y, and Z contains all information of the ECG, it may also be used to calculate a full 12-lead ECG in real time using a known algorithm. This way, the preferred embodiment may also continuously display a calculated averaged 12-lead ECG for every minute during the entire monitoring period of up to 48 hours in the format of a 12-lead ECG on central workstation 11. Based on the continuously stored X, Y and Z leads, a continuous calculated 12-lead ECG could also be displayed next to a chart with the occurrence of arrhythmias over a selectable range of hours marked as colored bars. The preferred embodiment may also produce a single page printout with a plurality of 12-lead ECG signals printed under each other. See, for example, FIG. 14.

The MIDA trends for each patient may be examined in detail one at a time on the workstation display. The trends of all patients may be monitored continuously on the central monitor using the format shown in FIG. 10.

Depending on the amount of memory provided, the MIDA recording may last, for example, only approximately 48 hours at one-minute intervals. After that, the memory is full and the recording is automatically stopped. Below is an exemplary chart comparing MIDA time intervals to maximum length of the recording.

| MIDA Time Interval | Maximum Length of Recording |
| --- | --- |
| 10 seconds | 8 hours |
| 15 seconds | 12 hours |
| 30 seconds | 24 hours |
| 1 minute | 48 hours (two days) |
| 2 minutes | 96 hours (four days) |
| 4 minutes | 192 hours (eight days) |

The arrhythmia full disclosure works differently, always keeping the most recent 24 hours in memory.

The setup menu contains a MIDA Relearn key to control the MIDA method. When the MIDA Relearn key is selected, the workstation display shows the latest ECG signals acquired with beat labels (beat labels are updated approximately 30 seconds). Every detected QRS complex is labelled with an "M" if it is recognized as a MIDA type of beat (matches the MIDA template).

The present MIDA Reference Complex is displayed to the left of the waveforms as scaler X, Y and Z leads. This is the actual, initial, averaged beat to which all subsequent beats will be compared when calculating the relative trend parameters.

The system provides a Restart MIDA key in the MIDA setup display for beginning the process over again. If the Restart MIDA key is selected, a warning message is displayed with options to cancel (No/Cancel) or proceed (Yes). Then a message "Selecting MIDA template, please wait for 20 seconds" is displayed with an option to cancel.

If the process is not cancelled, a suggested new template is displayed in a square for consideration by the user along with three keys for selection.

If the Yes key is selected, the entire previous MIDA recording is erased, the suggested template is accepted and the method is restarted. The display is reset, but with no MIDA Reference Complex displayed, since no new Reference Complex has yet been formed.

If the No key is selected, the template selection procedure is restarted and a message asking the user to wait for 20 seconds is displayed.

The MIDA system also includes a "MIDA Relearn" feature, the steps of which are identical to the Restart MIDA command described above except that the previously recorded and stored data is not erased.

This feature is appropriate when the MIDA analysis is no longer capable of tracking the ECG. MIDA relearn will find a new template for including ECG complexes in the analysis. (ECG changes always refer to the initial, reference ECG.)

The system also permits the user to review the MIDA Signal Status 107 included in the display, shown in FIG. 10, for each patient. The signal status for all patients is displayed in a Signal Status table when the Signal Status key in FIG. 9 is selected.

Below is a list of different possible MIDA signal status messages in order of priority. The line with message of highest priority is indicated with a red background.

1) No MIDA Recording possible with current patient cable. An 8-lead cable is needed for the MIDA recording. If a 5-lead cable is in use, this message is shown.

2) MIDA Recording Ended. The MIDA Recording may last for a maximum of 48 hours with one-minute intervals. When the memory is full, the recording is automatically stopped and this message is shown.

3) No MIDA Recording due to Spikes on signal. A signal spike is a very short disturbance of considerable signal strength. The origin of the disturbance may be pacemaker spikes, bad lead wires or electromagnetic radiation from other equipment. The system will automatically turn the spike filter off if the patient has got a pacemaker, as indicated in the Patient Info function.

4) NO MIDA Recording due to Noisy signal. Noise may be caused by many reasons. Bad patient electrode connection may be one reason. Line disturbances from other equipment close to the patient cable may be another.

5) No MIDA Recording due to Baseline Drift. If the baseline drift is too big, this may distort the ECG. To prevent this, the MIDA Recording is halted.

6) No MIDA Recording due to lead fail. One of the ECG leads is not working properly.

7) No MIDA Recording due to no reference type of beats. This message is active if the minimum number of reference type of beats was not received during the previous MIDA interval.

The system may also utilize a back position sensor. Since the heart is relatively mobile in the chest, it is only natural that it changes position within the chest when the patient changes position in the bed, e.g. from lying on the back to lying on the side. Since the electrodes record the electrical activity on the surface of the chest, the movement results in a change in the ECG. The influence of this change affects each of the MIDA parameters differently. Since ST-VM measures the strength of the ST deviation, regardless of direction, it is less sensitive than other "ordinary" ST measurements. The parameter QRS-VD is, however, very sensitive to these changes. A back position sensor makes it possible to tell if a change in the trend was caused by change of body position or not.

The Back Position Sensor connects to the junction block of the 8-lead ECG cable. The information from the back position sensor is recorded and displayed on a separate line below the trend graph. This line may have three colors indicating the following states:

| Color | State |
|---|---|
| Green | On Back |
| Yellow | Not On Back |
| Grey | No Trend available |

The MIDA trend may be displayed on the central monitor as described previously. The Trend key also arranges for the picture to be displayed on the display of the workstation for review.

Keys appear to the left allowing the user to select what trend will be displayed. These keys may be labelled MIDA and HR/PVC.

Up to four different trend curves may be displayed in the trend graph. To be able to tell the curves apart, they are displayed in different colors. The name of each trend curve is also written over the graph in the same color as the curve itself.

The system provides a cursor, controlled by the mouse, in order to, for example, mark points of special interest. (If points of special interest are marked in the trend curve, they may be of assistance when examining the corresponding 12-lead ECGs.) By pointing and clicking in the trend, the cursor is moved to the desired time. Alternatively, the cursor may be moved step by step by pressing the right and left arrows under Cursor labels on the bottom of the display of the trend graph. The system displays time of the trend graph corresponding to the position of the cursor on the top of the graph, both as time of day and time since admission. The system also displays the exact values of the parameters to the left and to the right of the time.

Points are marked by placing the trend cursor at the desired time and selecting the check key which is displayed between the arrows under the Mark label to the right under the graph. When the trend cursor is placed on a marked time, the system turns the check key to yellow.

The user can jump directly between separately marked times by selecting the right and left arrows under the Mark label. The system unmarks a time whenever the user presses the check key again.

The system also permits the user to change the parameters in the trend graph. (Users normally select the QRS-VD and ST-VM parameters for display in the trend graph. The MIDA analysis includes thirty parameters that are continuously calculated and stored.) The MIDA trend display contains keys under the Trend parameter label which select the axis to be affected (Le1=Left one, Le2=Left two, etc.). A table of different parameters will then be displayed in response to the selection of an axis. The user then selects the key of the desired new parameter to be trended. A Return key is selected to return to the graph.

The system further permits adjustment of the timescale of the trends to include the most interesting parts of the trends. Zoom keys are displayed, which, when selected, make it possible to enlarge certain parts of the trend curves. The system is set up so that "zooming" is centered around the cursor, which can be placed in the middle of the interesting part of the trend curves by pointing and clicking with the mouse. Every time the left "→←" zoom button is pressed, the curves around the cursor are expanded. The right "→←" zoom button has the reverse effect; it goes back and shows bigger portions of the curves.

The system also provides a Scale key, which when selected displays additional keys which enables the user to adjust the size of the displayed graph.

The height of the trend curve(s) may be increased or decreased by selecting arrows under the Max label to the left and to the right of the graph. The baseline offset may be adjusted by selecting the arrows under the Offset label.

After the scales have been changed, they may be reset to default at any time by pressing the Normal key.

Again, a Return key must be selected to return to the graph. The system further allows the time to be changed with a key displayed on the bottom right hand side. Clock time is the time of day (8:30 means eight thirty in the morning) while Relative time is time since admission (8:30 means that the patient has been monitored for eight and a half hours).

It is also a particular advantage of the system employing the method that a number of settings controlling the MIDA analysis may be adjusted to customize the analysis. The MIDA setup is available through the MIDA Setup key.

The different settings are described below, one by one. Each group of settings may be reset to default values individually by pressing the Normal key next to each group.

The MIDA interval is the time interval within which the MIDA analysis will produce new values. During each interval, all acquired ECGs of sufficient signal quality that match the initial reference ECG will be averaged to form an ECG with improved signal quality. At the end of the interval, the averaged ECG is used when calculating the MIDA parameters. The averaged ECG and the parameters values of every such interval is stored in the Acquisition Module for approximately 3000 intervals.

Short intervals (less than 1 minute) have the advantages of fast response to rapid ECG changes, but they also have more noise and result in a shorter total recording time.

Long intervals (more than 1 minute) have less noise and result in a longer recording time but they also respond slowly to rapid ECG changes. Generally, one minute intervals are recommended for CCU monitoring (infarction, unstable angina, etc.) and 15 second intervals are recommended for PTCA use. The default setting is preferably 1 minute.

To form an averaged ECG at the end of the intervals previously described, a minimum number of beats must have been included in the average. Too low a limit may result in poor signal quality. Too high a limit may result in difficulties reaching the limit with no calculated parameter values as a result. Naturally, the minimum number of beats required is dependent on the interval length. Recommended settings:

| MIDA interval | Minimum number of beats |
|---|---|
| 10 seconds | 1 beat |
| 15 seconds | 1 beat |
| 30 seconds | 2 beats |
| 1 minute | 2 beats (factory setting) |
| 2 minutes | 10 beats |
| 4 minutes | 10 beats |

If the signal quality of the acquired ECG is too poor, the ECG will not be used for MIDA analysis. This is to avoid false results —artifacts. Each ECG signal has to pass the following tests to be included in the MIDA analysis.

A signal spike is a very short disturbance of considerable signal strength. The origin of the disturbance may be electromagnetic radiation from other equipment, bad lead wires or pacemakers. The spike test may be turned on or off. When spikes are detected, the MIDA analysis is halted unless the patient has a pacemaker.

Noise may be caused by many reasons. Bad patient electrode connection may be one reason. Line disturbances from other equipment close to the patient cable may be another. The noise threshold may be set to 5, 10, 20, 50 or 100 micV or may be turned off. When excessive noise is detected, the MIDA analysis is halted. The default setting is 50 μV.

If the baseline variation is too big, this may distort the ECG. The baseline threshold may be set to 25, 50, 100, 200 or 400 micV/second or be turned off. When baseline variation is detected, the MIDA analysis is halted. The preferred default setting is 100 micv/sec.

The default settings may be selected by the user in a table default settings which is opened by selecting the System key and entering an access code. The table includes a save key and a cancel key which, when selected, respectively set the default settings or close the menu with no alterations to the default settings.

SECOND EMBODIMENT

A second embodiment of the invention may be used as a complement to a conventional monitoring system for enhanced monitoring and documentation of the ECG in terms of ischemia, infarction and arrhythmia.

This embodiment also has the advantages of ischemia monitoring with parameters reflecting the ECG changes in clear trend graphs, averaged 12-lead ECG acquisition, storage and display, arrhythmia detection, 24-hour full disclosure arrhythmia of all monitored patients, and 24-hour continuous 12-lead ECG stored for all monitored patients.

However, this embodiment does not contain a monitoring system with waveforms and arrhythmia alarms. Rather, it is a system for only monitoring ischemia and the course of various heart diseases. Waveforms and alarms are controlled and monitored using the conventional monitoring system.

It consists Of the elements shown in FIG. 7, except that instead of a bedside monitor, it has an Acquisition Module for each patient, connected via Ethernet to a central Server. The server displays and stores data from all connected Acquisition Modules. It is a supplement to a conventional monitoring system adding the functionality described with respect to the first embodiment.

The Acquisition Module works in parallel with the patient monitor of the conventional monitoring system. The ECG signal from the patient is fed into both the Acquisition Module as well as the patient monitor. The parallel connection is achieved with an adapter cable between the acquisition module and the patient monitor.

The Acquisition Module acquires the signal, converts it from analog to digital and performs ischemia and arrhythmia analysis. The Acquisition Module communicates with the central Server via an Ethernet connection on the back. It also includes a serial port for connection to other devices, such as the Hewlett Packard VueLink interface module.

FIG. 12 shows a face of an Acquisition Module. Element 121 is an ECG input for use with either 8-lead or 5-lead patient cables. Element 122 is a Signal out for connection to the ECG input of the conventional monitor. Element 123 is a torso with electrode indicators. Each electrode is indicated individually with a twinkling yellow light if the signal quality is poor or with a steady yellow light if the lead fails. When the signal quality is all right, all electrode indicators are off. Element 124 is a MIDA status indicator with a green and yellow indicator. The green indicator is on when MIDA analysis is running. If the MIDA analysis is not running for anyone of various reasons, the yellow indicator is on. Element 125 is a back position indicator. A back position sensor is a position sensitive device that may be used to record if the patient is lying on his back or not. This information may be useful when examining the most sensitive parameters such as QRS-VD of the MIDA analysis. When such a sensor is used, the back position indicator is green only when the patient is lying on his back. Element 126 is an event Mark key. When this key is pressed, an event mark in recorded by the system. Element 127 is a Pause key. The recording may be paused and resumed with this key. When paused, recording and analysis are temporarily halted. This is indicated with a yellow light behind the pause symbol. Element 128 is a Discharge Patient key. When this key is pressed, the current recording is terminated and the MIDA module is ready to start anew. Element 129 is a Main Power operation indicator. A green light indicates that the module is on, running on main power. Element 130 is a Battery Power operations indicator. A yellow light indicates (a warning) that the module is on, running on the internal battery for very limited time. Element 120 is an On/Off Switch. The module is turned on pressing the switch. The module is turned off by pressing the switch again.

The patient input of the MIDA Acquisition Module is of Type CF, it is defibrillation proof (it may remain connected to the patient during defibrillation), and the patient connector on the front is marked with the appropriate heart symbol.

The patient input of the MIDA Acquisition Module is designed to limit the current through the patient to a few microAmperes and to comply with the requirements for low leakage currents when connected to a conventional Monitoring System. If other equipment than the MIDA Acquisition Module is connected to the patient, it should be interconnected with an equipotential grounding cable. On the back of the MIDA Acquisition Module there is an equipotential grounding terminal for this purpose.

The following connections are provided on the rear (not shown) of the MIDA Acquisition Module:

AC in—to be connected to a grounded electrical AC source of 100 –240 V+−10%, 50–60 Hz.

Equipotential grounding terminal—used to obtain the same electrical earth reference when additional electrical equipment is used together with the MIDA Acquisition Module.

Ethernet—for connection to the Ethernet network.

RS-232 Serial communication—for connection to other devices, such as a Hewlett Packard VueLink module.

The Acquisition Module is equipped with an internal battery that is switched in as soon as the AC power is insufficient. The internal battery provides full operation for at least five minutes, when fully charged. When the MIDA Acquisition Module operates on the internal battery, a yellow LED is lit in the lower right corner of the front, under the battery symbol. The internal battery is recharged as soon as the AC power is back and the Module is on. Line power operation is indicated by a green LED in the lower right corner, under the AC symbol.

Workstation 11 also contains a 17" color monitor on which curves and data from one patient at one time may be brought up for examination. The workstation also contains a graphical interface with a mouse, which may be used to control the operation of up to two of the central monitoring units. However, the central monitors are not disturbed at all when the monitoring of one specific patient is controlled or examined at the workstation. All information presented on the workstation at any time may be printed on the laser printer.

A row of keys on the top of the workstation monitor allows selection and direct control of the monitoring of each patient. The keys are marked with an identification tag for each bed (normally 1, 2, 3 and so on). When a patient has been selected, the operator may control admission/discharge, alarm settings, waveforms monitored, and much more in a straightforward and easy manner using the graphical interface. A monitoring session may also be examined in detail in terms of ischemia, 12-lead ECGs and full disclosure arrhythmias.

When the ischemia trends are examined on the workstation, any one of 30 different calculated parameters may be examined over time. Interesting events may then be expanded on the screen and exact values corresponding to the events will be shown. Short events can be expanded to display a couple of minutes on the display even if the entire trend covers several days of monitoring.

The system in the preferred embodiment of the invention reduces the need for additional 12-lead ECGs. Minute-by-minute, derived 12-lead ECGs are automatically acquired and stored in the system. Several 12-lead ECGs may be superimposed from different times in order to plot gradual changes. By pointing out interesting ischemic events in the ischemia graphs, the corresponding 12-lead ECGs may be displayed, superimposed or printed on the laser printer, if desired. Thus the morphologic nature of the ischemic changes may be examined in real time, i.e., during thrombolytic therapy or unstable angina.

Workstation 11 also contains a complete 24-hour full disclosure arrhythmia review function. The arrhythmia graph is presented on the lower half of the workstation display, with the arrhythmias plotted as colored dots or lines depending on the duration of the arrhythmias. The corresponding ECG is displayed on the upper half of the display. Every single heartbeat during the previous 24 hours can be displayed for each monitored patient by pointing out either the arrhythmia of interest or the desired time of day.

The system also contains a data storage unit for storing all data from the monitoring session for future examination. A stored recording may be examined on the workstation in exactly the same way as currently monitored patients.

The preferred embodiment of the invention described above uses a complete networking system for a number of patients to perform the following analysis and monitoring. However, use of the invention is not limited to the preferred embodiment of the invention described above. For example, the method may be used in a this method of analysis and monitoring may be technically implemented using different hardware, system architecture or a special program code in a different program coding. The method employing the invention may, for example, be used in a stand-alone system for a single patient.

The method may also be used in an ambulatory application. In such an application, ECG signals are recorded over a long period of time by a recording device worn or carried by the patient. The recorded signals are later retrieved for printout and analysis. The signals may then be analyzed according to the method described here below.

In a telemetry application, the patient carries a small transmitter which transmits the ECG signals to a receiver where the signals are displayed in real time. The ECG signals received by the telemetry system are then analyzed according to the following method.

The invention is not limited to the systems and methods illustrated in the drawings and described above. Modifications and variations are possible within the inventive concept. The disclosure should not be construed as limiting the scope of the following claims, which specifically define the invention.

What is claimed is:

1. A myocardial ischemia and infarction analysis and monitoring method comprising the steps of:

receiving a number of ECG signals relating to the heartbeat of at least one patient;

converting the received number of ECG signals into three perpendicular ECG signals;

determining, for each occasion that a number of ECG signals is received, whether or not the number of ECG signals correspond to a normal heartbeat;

determining, for each occasion that a number of ECG signals is received, whether or not the signal quality of the ECG signals exceeds a minimum level;

determining an average heartbeat from only those ECG signals which correspond to a normal heartbeat and for which the signal quality exceeds a minimum level;

calculating a plurality of parameters related to the ischemic condition of each patient from said number of ECG signals;

generating electric signals representative of the value of said plurality of parameters related to the ischemic condition of each patient;

storing said electric signals representative of the value of said plurality of parameters related to the ischemic condition of each patient in a memory; and repeating the steps of determining said average heartbeat, calculating said plurality of parameters, generating electric signals and storing said electric signals for as long as ECG signals continue to be received or until the memory is full.

2. A myocardial ischemia and infarction analysis and monitoring method as recited in claim 1, which presents said plurality of parameters in trend graphs having time along the horizontal axis and the value of the parameter along the vertical axis.

3. A myocardial ischemia and infarction analysis and monitoring method as recited in claim 1, which stores the the average heartbeat in the form of said three perpendicular ECG signals.

4. A myocardial ischemia and infarction analysis and monitoring method as recited in claim 1, which further comprises the steps of:

continuously recording said three perpendicular ECG signals; and calculating a second number of ECG signals from said three perpendicular ECG signals in response to a request by a user.

5. A myocardial ischemia and infarction analysis and monitoring method as recited in claim 4, which comprises the further step of displaying said second number of ECG signals in response to a user request.

6. A myocardial ischemia and infarction analysis and monitoring method as recited in claim 4, wherein said second number of ECG signals is twelve.

7. A myocardial ischemia and infarction analysis and monitoring method as recited in claim 1, wherein at least one of said plurality of parameters is a ST vector magnitude parameter.

8. A myocardial ischemia and infarction analysis and monitoring method as recited in claim 1, wherein at least one of said plurality of parameters is a STC vector magnitude parameter.

9. A myocardial ischemia and infarction analysis and monitoring method as recited in claim 1, wherein at least one of said plurality of parameters is a QRS vector difference parameter.

10. A myocardial ischemia and infarction analysis and monitoring method as recited in claim 1, which comprises the further step of:

storing those ECG signals determined to correspond to a dominant heartbeat;

wherein said step of determining an average heartbeat is repeated at the end of each interval in which a number of ECG signals corresponding to a dominant heartbeat is received at least a predetermined number of times and includes said number of ECG signals corresponding to a dominant heartbeat received during said interval, and wherein said steps of calculating said plurality of parameters and generating electric signals are carried out using the most recently determined average heartbeat.

11. A myocardial ischemia and infarction analysis and monitoring method as recited in claim 1, which comprises the further steps of:

displaying at least one of said plurality of parameters for each patient on a respective patient monitor substantially in real time;

receiving and storing data from each patient monitor at a central location, said data including said at least one of said plurality of parameters;

displaying said at least one of said plurality of parameters received from each patient monitor; and printing information related to said data received from each patient monitor.

12. A myocardial ischemia and infarction analysis and monitoring system comprising:

at least one patient monitor, each patient monitor having an analyzing circuit for receiving a number of ECG signals relating to the heartbeat of a corresponding patient, for determining, for each occasion that the number of ECG signals is received, whether or not the number of ECG signals correspond to a normal heartbeat, for determining, for each occasion that the number of ECG signals is received, whether or not the signal quality of the ECG signals exceeds a minimum level, for determining an average heartbeat from only those ECG signals which correspond to a normal heartbeat and for which the signal quality exceeds the minimum level, and for calculating therefrom a plurality of parameters related to the ischemic condition of the corresponding patient, and a display for displaying at least one of said plurality of parameters substantially in real time;

a central workstation for receiving and storing data from each patient monitor, said data including said at least one of said plurality of parameters;

a central monitoring unit for simultaneously displaying said at least one of said plurality of parameters received from each patient monitor; and a network for transferring data between each patient monitor, said central workstation, and said central monitoring unit.

13. A myocardial ischemia and infarction analysis and monitoring system as recited in claim 12, wherein said at least one of said plurality of parameters includes a ST vector magnitude parameter.

14. A myocardial ischemia and infarction analysis and monitoring system as recited in claim 12, wherein said at least one of said plurality of parameters includes a STC vector magnitude parameter.

15. A myocardial ischemia and infarction analysis and monitoring system as recited in claim 12, wherein said at least one of said plurality of parameters includes a QRS vector difference parameter.

16. A myocardial ischemia and infarction analysis and monitoring system as recited in claim 12, wherein said central workstation comprises a CPU, a data storage unit, a display, a graphical interface, and a printer for printing information related to said data received from each patient monitor.

17. A myocardial ischemia and infarction analysis and monitoring system as recited in claim 12, which further comprises a printer which produces a single page printout with a plurality of ECG signals printed under each other.

18. A myocardial ischemia and infarction analysis and monitoring system comprising:

at least one patient monitor, each patient monitor having an analyzing circuit for receiving a number of ECG signals relating to the heartbeat of a corresponding patient and calculating therefrom a plurality of parameters related to the ischemic condition of the corresponding patient, and a display for displaying at least one of said plurality of parameters substantially in real time;

a central workstation for receiving and storing data from each patient monitor, said data including said at least one of said plurality of parameters;

a central monitoring unit for simultaneously displaying said at least one of said plurality of parameters received from each patient monitor; and a network for transferring data between each patient monitor, said central workstation, and said central monitoring unit;

wherein the analyzing circuit of each patient monitor continuously records a number of perpendicular lead signals corresponding to said number of ECG signals and calculates a second number of ECG signals from said recorded number of perpendicular lead signals in response to a request by a user.

19. A myocardial ischemia and infarction analysis and monitoring system as recited in claim 18, wherein each patient monitor continuously displays said second number of ECG signals.

20. A myocardial ischemia and infarction analysis and monitoring system as recited in claim 18, wherein said second number of ECG signals is twelve.

* * * * *

US005520191C1

(12) EX PARTE REEXAMINATION CERTIFICATE (5490th)
United States Patent
Karlsson et al.

(10) Number: US 5,520,191 C1
(45) Certificate Issued: Sep. 5, 2006

(54) MYOCARDIAL ISCHEMIA AND INFARCTION ANALYSIS AND MONITORING METHOD AND APPARATUS

(75) Inventors: Per Karlsson, Taby (SE); Gunilla Lundahl, Lidingo (SE); Michael Oljemark, Saltsjo-Boo (SE); Johan Ubby, Vaxholm (SE)

(73) Assignee: Ortivus AB, Taby (SE)

Reexamination Request:
No. 90/005,822, Sep. 19, 2000

Reexamination Certificate for:
Patent No.: 5,520,191
Issued: May 28, 1996
Appl. No.: 08/320,511
Filed: Oct. 7, 1994

(51) Int. Cl.
*A61B 5/0472* (2006.01)

(52) U.S. Cl. ........................................ 600/515; 600/512
(58) Field of Classification Search .................. None
See application file for complete search history.

(56) References Cited

U.S. PATENT DOCUMENTS

| 4,216,526 A | 8/1980 | Karwowski |
| 4,570,225 A | 2/1986 | Lundy ........................ 600/300 |
| 4,924,875 A | 5/1990 | Charmoun .................. 600/509 |
| 5,083,571 A | 1/1992 | Prichep |

FOREIGN PATENT DOCUMENTS

| DE | 4243889 | 7/1993 |

OTHER PUBLICATIONS

H. Rix et al. "High Resolution ECG System for Micropotentials Analysis and Shape Classification" Proceedings of the Annual International Conference of the IEEE EMBS, col. 13, No. 2, Nov. 3, 1991, pp. 641–642.
"A Clinical Introduction to the MIDA Concept Manual", 1993, pp. 5–36.
"The MIDA CoroNet Product Line, Product Information and Pricelist", Jun., 1993, pp. 3–21.
"MIDA 1200 CoroNet Central Unit", Aug., 1992.
"MIDA 1100 Bedside Patient Monitor", Aug., 1992.
"MIDA 1000 Operator's Manual", May 1989, pp. 1–111.
Working with Ischemic Patients, pp. 3–7.
"Operations Manual MIDA™ CoroNet Central", English Edition, Apr., 1992, vol. 4.0, pp. 3–45.
"Coronary Artery Disease", 1991, vol. 2, pp. 43–52.
"66th Scientific Sessions Abstract Form", Sven Hauck, Franz–Volhard–Klinik, American Heart Association, Nov. 8–11, 1993.
"Dynamic QRS Complex and ST Segment Vectorcardiographic monitoring can identify vessel patency in patients with acute myocardial infarction treated with reperfusion therapy", "American Heart Journal", M. Dellborg, E. Topol and K. Swedberg, Oct., 1991, vol. 122 pp. 943–948.
"Early Evaluation of Infarct Size by Vectorcardiographic Monitoring During the Early Hours of Acute Myocardial Infarction", European Society of Cardiology, S. Flochlay, P.G. Steg, JM. Juliard, D. Himbert, T. Laperche, R. Gourgon, Aug. 30–Sep. 1992.
"Dynamic Electrocardiographic Monitoring can Determine Early Vessel Patency After Reperfusion Therapy for Acute Myocardial Infarction", M. Dellborg, M. van den Brand, R. Dietz, S. Sen, M. Simoons, G. Steg, K. Swedborg on behalf of VERMUT–study. University of Goteborg, Goteborg, S. Operations Manual MIDA™ Bedside, English Edition, Apr., 1994, vol. 4.0, pp. 3–71.

(Continued)

*Primary Examiner*—Carl Layno

(57) ABSTRACT

A cardiac monitoring method and system provides advanced ischemia and infarction analysis and monitoring. Advanced calculations are performed on ECG signals to obtain parameter values relating to myocardial ischemia and infarction. Dominant heart beats are averaged to form a smooth beat, which is analyzed to determine the parameter values continuously and in real-time. The result of each analyzed time interval is presented as points in a trend graph on a monitoring display. All calculations are performed on-line and the trend curves are updated immediately.

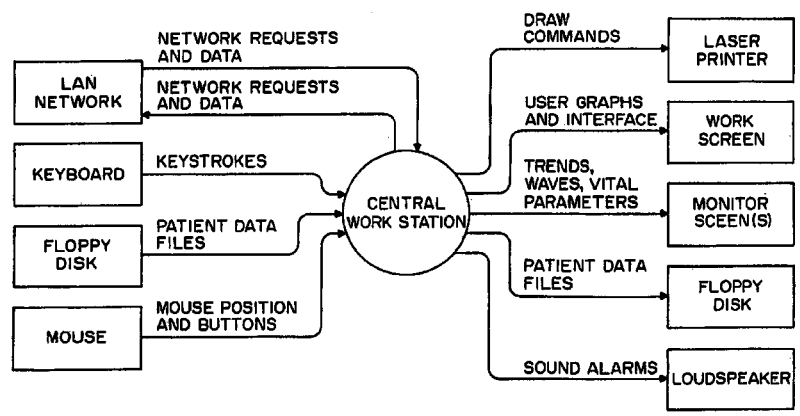

OTHER PUBLICATIONS

"User's Reference Manual to the MIDA™ System", English Edition, Jun. 1994, vol. 0.3, pp. 3–73.

"High Resolution ECG System for Micropotentials Analysis and Shape Classification", H. Rix, A. Varenne, A. Bally and E. Thierry, 1991, vol. 13, pp. 641–642.

"On Deriving the Electrocardiogram from Vectorcardiographic Leads", G.E. Dower, H.B. Machado, J.A. Osborne, Clinical Cardiology, 1980, vol. 3, 87–95.

"Acute Myocardial Infarction and Bundle–Branch Block–High Diagnostic Accuracy With Computerized Continuous, On–line Vectorcardiographic Monitoring", P. Eriksson, M. Dellborg, M. Riha, K. Swedberg, European Heart Journal, 1990.

Ischaemic Heart Disease and the Changes in the QRS and ST Segments During Exercise: "A Pilot Study With a Novel VCG System", Pilhall M, Riha M, Jern S, Clinical Physiology, 1992, vol. 12, pp. 209–223.

"Assessment of Reperfusion After Thrombolytic Therapy For Myocardial Infarction", Anita Zeiler Arnold, DO, and Eric J. Topol, MD, American Heart Journal, 1992, vol. 124, pp. 441–447.

"Changes in the QRS Segment During Exercise:—Effects of Acute Beta–Blockade with Propranolol", Pilhall M, Riha M, Jers S, Clinical Physiology, 1993, vol. 13, pp. 113–131.

"Impact of Early Thrombolysis on Chest Pain Score Reflecting Myocardial Ischemia in Relation to Various Markers of Ischemic Damage", J. Herlitz, M. Dellborg, M. Hartford, B. Karlson, T. Karlsson, International Journal of Cardiology, 1993, vol. 41, pp. 123–131.

"Ischemia—and Reperfusion—Induced Transient QRS–Vector Changes: Relationship to Size of the Ischemic Territory", Näslund U, Häggmark S, Johansson G, Reiz S, Cardiovascular Research, 1993, vol. 27, pp. 327–333.

"Quantification of Myocardium at Risk and Detection of Reperfusion by Dynamic Vectorcardiographic ST–Segment Monitoring in a Pig Occlusion—Reperfusion Model", Näslund U, Häggmark S, Johansson G, Reiz S, Cardiovascular Research, 1993, vol. 27, pp. 2170–2178.

"ECG Changes During Myocardial Ischemia, Differences Between Men and Women", J. Herlitz, MD, M. Dellborg, MD, H. Emanuelsson, MD, K. Swedberg, MD, Journal of Electrocardiology, 1994, vol. 27 (suppl).

"Prognostic Information From On–line Vectorcardiology in Acute Myocardial Infarction", Peter Lundin, MD, Sven V Eriksson, MD, Lars–Erik Stranberg, MD, and Nina Rehnqvist, MD, PhD, American Journal of Cardiology, 1994, vol. 74, pp. 1103–1108.

"Prognostic Information From On–line Vectorcardiology in Unstable Angina Pectoris", Peter Lundin, Sven V Eriksson, Mia Frederiksson, Nina Rehnqvist, Cardiology, 1995, vol. 86, pp. 60–66.

"Dynamic QRS–Complex and ST–Segment Monitoring in Acute Myocardial Infarction During Recombinant Tissue–Type Plasminogen Activator Therapy", Dellborg M, Riha M, Swedberg K, for the TEAHAT study–group, American Journal of Cardiology, 1991, vol. 67, pp. 343–349.

"Continuous Vectorcardiology in Patients With Chest Pain Suggestive of Acute Ischemic Heart Disease (IHD)", Peter Lundin, Sven V Eriksson, Nina Rehnqvist, Cardiology 1992, vol. 81, pp. 145–156.

"Dynamic Changes of the QRS Complex in Unstable Angina Pectoris", Dellborg M, Gustaffosson G, Riha M, Swedberg K, International Journal of Cardiology, 1992, vol. 36, pp. 151–162.

"Silent Myocardial Ischemia During Coronary Angioplasty", Mikael Dellborg MD, Håkan Emanuelsson, MD, Karl Swedberg, MD, Cardiology, 1993, vol. 82, pp. 325–334.

"Early Electrocardiographic Changes in Acute Myocardial Infarction Treated by Streptokinase of Alteplase: A Randomized Study With Dynamic, Multi–lead, Electrocardiographic Monitoring", Mikael Dellborg MD, Ann–Marie Svensson RN, Mats Johansson MD, Karl Swedberg MD, Cardiology, 1993, vol. 82, pp. 369–376.

"Electrocardiographic Assessment of Infarct Size: Comparison between QRS scoring of 12–lead Electrocardiology and Dynamic Vectorcardiography", Mikael Dellborg, Johan Herlitz, Martin Risenfors and Karl Swedberg, International Journal of Cardiology, 1993, vol. 40, pp. 167–172.

"A Clinical Appraisal of the Vectorcardiogram in Myocardial Infarction. II The Frank System", Hugenholtz PG, Forkner CE Jr, Levine HD, Circulation, 1961, vol. 24, pp. 825–850.

"Correlation of Vectorcardiographic Criteria For Myocardial Infarction With Autopsy Findings", Gunner RM, Pietras RJ, Blackaller J, Damun SE, Szanto DB, Tobin JR, Circulation, 1967, vol. 35, p. 158–171.

"A Lead Synthesizer for the Frank System to Simulate the Standard 12–Lead Electrocardiogram", G.E. Dower, Journal of Electrocardiology, 1968, vol. 1, pp. 101–116.

"Comparative Quantitative Analysis of the Electrocardiogram and the Vectorcardigram", McConahay DR, McCallister BD, Hallerman FJ, Smith RE, Circulation, 1970, vol. 42, p. 245–259.

"Electrocardiogram and Vectorcardiogram in Myocardial Infarction", Levine HD, Young E, Williams RA, 1972, Circulation, vol. 45 p. 457–470.

"Vectorcardiographic Criteria for the Diagnosis of Anterior Myocardial Infarction", Starr JW, Wagner GS, Draffin RM, Reed JB, Walston A, Behar VS, 1976, Circulation, vol. 53, pp. 229–234.

"XYZ Data Interpreted by a 12–Lead Computer Program Using the Derived Electrocardiogram", G.E. Dower, Hilario Bastos Machado, J. Electrocardiogram. 1979, vol. 12, pp. 249–261.

"Comparative Accuracy of Electrocardiographic and Vectorcardiographic Criteria for Inferior Myocardial Infarction", Hurd II HP, Starling MR, Crawford MH, Dlabal PW, O'Rourke RA, 1981, Circulation, vol. 63, pp. 1025–1029.

"Sensitivity for Telemed Diagnosis of Myocardial Infarction by Use of 12–Lead Electrocardiogram Derived from Frank XYZ Leads", Bruce RA, Belanger L, Blackmon JR, Trimble S., Journal of Electrocardiology, 1982, vol. 15, pp. 157–163.

"Continuous Vectorcardiography in Acute Myocardial Infarction. Natural Course of ST and QRS Vectors", Sederholm M, Erhardt L, Sjögren A, International Journal of Cardiology, 1983, vol. 4, pp. 53–63.

"Relation Between ST and QRS Vector Changes and Myoglobin Release in Acute Myocardial Infarction", Sederholm M, Sylven C, Cardiovascular Research, 1983, vol. 17, pp. 589–594.

"Quantitative Assessment of Myocardial Ischemia and Necrosis by Continuous Vectorcardiography and Measurement of Creatine, Kinase Release in Patients", Sederholm M, Grottum P, Erhardt L, Kjekshus J, Circulation, 1983, vol. 5, pp. 1006–1012.

"Reduction of Infarct Size With the Early Use of Timolol in Acute Myocardial Infarction", The International Collaborative Study Group (Coordinator M. Sederholm), New England Journal of Medicine, 1984, vol. 310, pp. 9–15.

"The ECDG: A Derivation of the ECG from VCG Leads", Gordon E. Dower, Journal of Electrocardiology, 1984, vol. 17, pp. 189–191.

"Real–Time Serial Analysis of Infarctional Changes in the Vectorcardigan", Grööttum P. Computer and Biomedical Research, 1985, vol. 18, pp. 205–219.

"Course of Chest Pain and its Relation to CK Release and ST/QRS Vector Changes in Patients With Acute Myocardial Infarction Randomized to Treatment With Intravenous Timilol or Placebo", Sederholm M, Gröttum P, Kjekshus J, Erhardt L, American Heart Journal, 1985, vol. 110, pp. 521–528.

"When is the Vectorcardiogram Superior to the Scalar Electrocardiogram?", Chou TC, Journal of the American College of Cardiology, 1986, vol. 8, pp. 791–799.

"A Comparison of Cumulated CK Release With Three Vectorcardiographic Methods of Estimating Myocardial Infarct Size", Grötten P, Kjekshus JK, Journal of Electrocardiology, 1986, vol. 19, pp. 337–345.

"Evolution of Vectorcardiographic QRS Changes During Myocardial Infarction in Dogs and in Their Relations to Infarct Size", Gröttum P, Mohr B, Kjekshus J, Cardiovascular Research, 1986, vol. 20, pp. 108–116.

"Comparison of the Classification Ability of the Electrocardiogram and Vectorcardiogram", Jos L. Willems MD, Emmanuel Lessaffre, Dsc, and Jos Pardaens Dsc., American Journal of Cardiology, 1987, vol. 59, pp. 119–124.

"Quantitative and Temporal Relation Between the Release of Myoglobin and Creatine Kinase and the Evolution of Vectorcardiogram Changes During Acute Myocardial Infarction in Man", Gröttum P, Sederholm M, Kjekshus K, Cardiovascular Research, 1987, vol. 21, pp. 652–659.

"Bundle–Branch Block and Acute Myocardial Infarction–Predictive Value of Initial ST Vector Magnitude", P. Erikkson, M. Dellborg, M. Riha, K. Swedberg, 1991, European Heart Journal, vol. 12, p. 666.

"Early ST–Segment Variability in Acute Myocardial Infarction Indicates a Large Infarction and is not Influenced by Treatment with Thrombolytics", M. Dellborg, K. Swedberg, European Heart Journal, 1991, vol. 12, p. 771.

"Changes of the QRS–Complex are More Sensitve than ST–Segment Devations in the Detection of Temporary Myocardial Ischemia During PTCA", S. Hauk, R. Lechenmayer, D. Höhnlein, K.J. Osterziel, R. Willenbrock, G. Claus, D. Gulba, R. Dietz, Circulation, 1993, vol. 88, p. 1636.

"Noninvasive Assessment of Reperfusion and Reocclusion After Thrombolysis in Acute Myocardial Infarction", Peter Klootwijk MD, Christa Cobbaert PhD, Paolo Fioretti MD, Peter Paul Kint RN and Maarten L. Simoons MD, American Journal of Cardiology, vol. 72, 1993, pp. 75G–84G.

"Computerized Vectorcardiography for Improved Perioperative Cardiac Monitoring in Vascular Surgery", Gannedahl PE, Edner M, Ljungqvist OH, Journal of the American College of Surgeons, 1996, vol. 182, pp. 530–536.

"The Image Surface of a Homogeneous Torso", Frank E., American Heart Journal, 1954, vol. 47, pp. 757–768.

"Absolute Quantitative Comparison of Instantaneous QRS Equipotentials on a Normal Subject with Dipole Potentials on a Homogenous Torso Model", Frank E., Circulation Research, 1955, vol. 3, pp. 243–251.

"An Accurate, Clinically Practical System For Spatial Vectorcardiography", Frank E., Circulation, 1956, vol. 13, pp. 737–749.

"The Importance of Derived 12–Lead Electrocardiography in the Interpretation of Arrythmias Detected by Holter Recording", Pablo Denes MD, American Heart Journal, 1992, vol. 124, pp. 905–911.

"Transient Exacerbation of ST–Segment Evaluation Upon Reperfusion in acute Myocardial Infarction", G. Steg, M. Dellborg, M. Simoons, Journal of Electrocardiology, 1994, vol. 26 (suppl), p. 156.

"Dynamic Vectorcardiographic Monitoring in the Coronary Care Unit—The Göteborg Experience", Ann–Marie Svensson, Mikael Dellborg, Karl Swedberg, European Heart Journal, 1991, vol. 12, p. 1579 (abstr).

"Comparison Using Dynamic Vectorcardiography and MIBI SPECT of ST–Segment Changes and Myocardial MIBI Uptake During Percutaneous Transluminal Coronary Angioplasty on the Left Anterior Descending Coronary Artery", P.G. Steg MD, M. Faraggi MD, PhD, D. Himbert MD, J–M Juliard MD, A. Cohen–Solal MD, R. Lebtahi MD, R. Gourgon MF and D. Le Guludec MD, American Journal of Cardiology, 1995, vol. 75, pp. 998–1002.

"Dynamic On–Line Vectorcardiography Improves and Simplifies In–Hospital Ischemia Monitoring of Patients With Unstable Angina" Mikael Dellborg MD, Klas Malmberg MD, Lars Ryden MD, FACC, Ann–Marie Svensson RN, Karl Swedberg MD, FACC, Journal of the American College of Cardiology, 1995, vol. 26, pp. 1501–1507.

"Minimal Influence of Anaesthesia and Abdominal Surgery on Computerized Vectorcardiography Recordings", P. Gannedahl, M. Edner, S.G.E. Lindahl and O. Ljungqvist, Acta Anaesthesiologica Scandinavica, 1995, vol. 39, pp. 71–78.

"Continuous Vectorcardiographic Changes in Relation to Scintigraphic Signs of Reperfusion in Patients with Acute Myocardial Infarction Receiving Thrombolytic Therapy", P. Juhlin, P–A Boström, O. Hansen, H. Diemer, M. Feitag, B. Lilja and L. Erhardt, Journal of Internal Medicine, 1996, vol. 259, pp. 35–41.

"Vectorcardiographic Monitoring to Assess Early Vessel Patency After Reperfusion Therapy for Acute Myocardial Infarction. The VERMUT Trial", M. Dellborg, P.G. Steg, M. Simoons, R. Dietz, S. Sens, M. van den Braud, U.Lotze, S. Hauck, R. van den Wieken, D. Himbert, A–M. Svensson and K. Swedberg, European Heart Journal, 1995, vol. 16, pp. 21–29.

"On–Line Computerized Vectorcardiography Monitoring of Myocardial Ischemia During Coronary Angioplasty: Comparison with 12–Lead Electrocardiography", S. Jensen, G. Johansson, G. Osterman, S. Reiz and Ulf Näslund, Coronary Artery Disease, 1994, vol. 5, pp. 507–514.

"Dynamic QRS–Complex and ST–Segment Monitoring by Continuous Vectorcardiography During Coronary Angioplasty", M. Dellborg, H. Emanuelsson, M. Riha and K. Swedberg, Coronary Artery Disease, 1991, vol. 2, pp. 43–52.

"Changes in QRS Segments During Exercise in Relation to Scintigraphic Myocardial Perfusion Defects: A Multivariate Analysis", M. Pilhall, L. Jarneborn, M. Riha and Sverker Jern, Current Science, 1993, vol. 4, pp. 87–99.

"Increased Rate of Evolution of QRS Changes in Patients With Acute Myocardial Infarction—Results from the Vermut Study", M. Dellborg, P. Gabriel Steg, M. Simoons, R. Dietz, S. Sen, M. van den Brand, U. Lotze, S. Hauck, J. Juliard and K. Swedberg, Journal of Electrocardiography, 1993, vol. 26, pp. 244–248.

"Dynamisk Kontinuerlig Vektokardiografi", J. Markenvard and M. Dellborg, Ugeskr Leger, 1992, vol. 17, pp. 2296–2300.

"Continuous Vectorcardiography in Cardiac Surgery: Natural Course of Vector Changes and Relationship to Myocardial Oxygen Uptake", O. Wesslen, R. Ekroth, P. Joachimsson, L. Nordgren, S. Nystrom and H. Tyden, Scan J. Thor Cardovascular Surgery, 1991, vol. 25, pp. 45–50.

"Myocardial Recovery After Cardiac Surgery: A Study of Haemodynamic Performance and Elecrophysiolofy During the First 18 Postoperative Hours", O. Wesslen, J. van der Linden, R. Ekroth, P. Joachimsson, L. Nordgren and S. Nystrom, Journal of Cardiothoracic Anesthesia, 1990, vol. 6, pp. 672–680.

"Ischaemia Detected by Continuous On–Line Vectorcardiographic Monitoring Predicts Unfavourable Outcome in Patients Admitted with Probable Unstable Coronary Disease", K. Anderson, P. Eriksson and M. Dellborg, Coronary Artery Disease, 1996, vol. 7, pp. 753–760.

"Exercise–induced QRS Changes in Healty Men and Women: A Multivariate Analysis on their Relation to Background Data and Exercise Performance", M. Pilhall, M. Riha and S. Jern, European Heart Journal, 1992, vol. 13, pp. 1317–1324.

Vectorcardiographic Monitoring to Assess Early Vessel Patency After Reperfusion Therapy for Acute Myocardial Infarction. The Vermut Trial, M. Dellborg, P.G. Steg, M. Simoons, R. Dietz, S. Sens, M. van der Brand, U. Lotze, S. Hauck, R. van der Wieken, D. Himbert, A–M. Svensson and K. Swedberg, European Heart Journal, 1995, vol. 16, pp. 21–29.

"Thrombin Inhibition with Inogatran for Unstable Angina Pectoris: Evidence for Reactivated Ischemia After Cessation of Short–Term Treatment", K. Anderson, M. Dellborg, H. Emanuelsson, L. Grip and K. Swedberg, Coronary Artery Disease, 1996, vol. 7, pp. 673–681.

"Calculated 12–Lead ECG Derived from Vector ECG (Frank) as Compared with Traditionally Register 12–Lead ECG", E. Lofsjogard–Nilsson, Dep. of Clinical Physiology, Karolinska Hospital, Stockholm Sweden, Journal of Electrocardiology, 1990, vol. 23, p. 210.

"Ischemia Monitoring With On–Line Vectorcardiography Compared With Results From a Predischarge Exercist Test in Patients with Acute Ischemic Heart Disease", P. Lundin, J. Jensen, N. Rehnqvist and S. Eriksson, Journal of Electrocardiology, 1995, vol. 28. pp. 277–285.

"Tailored Thrombolytic Therapy", M. Simoons and A. Arnold, Circulation, 1993, vol. 88, pp. 2556–2564.

"Sleep Apnoea and Nocturnal Angina", K. Franklin, J. Nilsson, C. Sahlin and U. Näslund, 1995, vol. 345, pp. 1085–1087.

"Noninvasive Assessment of Speed and Stability of Infarct–related Atery Reperfusion: Result of the Gusto St Segment Monitoring Study", A. Langer, MD, FACC, M. Krucoff, MD, FACC, P. Klootwijk, MD, R. Veldkamp, MD, M. Simoons, MD, FACC, C. Granger, MD, FACC, R. Califf, MD, FACC, P. Armstron, MD FACC, for the GUSTO Investigators, 1995, vol. 25, pp. 1552–1557.

"Electrocardiographic Evidence for Reperfusion–induced Ischemia after Thrombolysis or Direct Angioplasty for Acute Infarction", P.G. Steg, S. Flochlay, D. Himbert, JM. Juliard, R. Gourgon, 1992, European Herart Journal, vol. 13, p. 1093.

"MIDA Bedside Operations Manual", English Edition 3.3, Aug. 24, 1993, pp. 2–65.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 18–20 is confirmed.

Claims 1 and 12 are determined to be patentable as amended.

Claims 2–11 and 13–17, dependent on an amended claim, are determined to be patentable.

1. A myocardial ischemia and infarction analysis and monitoring method comprising the steps of:
   receiving a number of ECG signals relating to the heartbeat of at least one patient;
   converting the received number of ECG signals into three perpendicular ECG signals;
   determining, for each occasion that a number of ECG signals is received, whether or not the [number of] *three perpendicular* ECG signals correspond to a normal heartbeat;
   determining, for each occasion that a number of ECG signals is received, whether or not the signal quality of the *three perpendicular* ECG signals exceeds a minimum level;
   determining an average heartbeat from only those *three perpendicular* ECG signals which correspond to a normal heartbeat and for which the signal quality exceeds a minimum level;
   calculating a plurality of parameters related to the ischemic condition of each patient from said [number of] *three perpendicular* ECG signals;
   generating electric signals representative of the value of said plurality of parameters related to the ischemic condition of each patient;
   storing said electric signals representative of the value of said plurality of parameters related to the ischemic condition of each patient in a memory; and
   repeating the steps of determining said average heartbeat, calculating said plurality of parameters, generating electric signals and storing said electric signals for as long as ECG signals continue to be received or until the memory is full.

12. A myocardial ischemia and infarction analysis and monitoring system comprising:
   at least one patient monitor, each patient monitor having an analyzing circuit for receiving a number of ECG signals relating to the heartbeat of a corresponding patient, *for converting the received number of ECG signals into three perpendicular ECG signals,* for determining, for each occasion that the number of ECG signals is received, whether or not the [number of] *three perpendicular* ECG signals correspond to a normal hearbeat, for determining, for each occasion that the number of ECG signals is received, whether or not the signal quality of the *three perpendicular* ECG signals exceeds a minimum level, for determining an average heartbeat from only those *three perpendicular* ECG signals which correspond to a normal heartbeat and for which the signal quality exceeds the minimum level, and for calculating [therefrom] *from the three perpendicular ECG signals* a plurality of parameters related to the ischemic condition of the corresponding patient, and a display for displaying at least one of said plurality of parameters substantially in real time;
   a central workstation for receiving and storing data from each patient monitor, said data including said at least one of said plurality of parameters;
   a central monitoring unit for simultaneously displaying said at least one of said plurality of parameters received from each patient monitor; and
   a network for transferring data between each patient monitor, said central workstation, and said central monitoring unit.

* * * * *